US008329096B2

(12) United States Patent
Elrod et al.

(10) Patent No.: US 8,329,096 B2
(45) Date of Patent: Dec. 11, 2012

(54) SYSTEMS AND METHODS FOR DETECTING DESCENTED MATERIAL

(75) Inventors: Scott A. Elrod, Angleton, TX (US); Peter C. Rooney, Lake Jackson, TX (US)

(73) Assignee: Parah, LLC, Angleton, TX (US)

( * ) Notice: Subject to any disclaimer, the term of this patent is extended or adjusted under 35 U.S.C. 154(b) by 0 days.

(21) Appl. No.: 12/456,944

(22) Filed: Jun. 24, 2009

(65) Prior Publication Data

US 2010/0107991 A1    May 6, 2010

Related U.S. Application Data

(63) Continuation-in-part of application No. 12/326,240, filed on Dec. 2, 2008, now Pat. No. 8,187,533, and a continuation-in-part of application No. 11/714,083, filed on Mar. 5, 2007, now abandoned, and a continuation-in-part of application No. 11/018,620, filed on Dec. 21, 2004, now Pat. No. 7,939,015.

(51) Int. Cl.
*A61L 2/24* (2006.01)

(52) U.S. Cl. .............................. 422/3; 422/5

(58) Field of Classification Search .................. 422/3, 5, 422/105, 107, 108, 119; 340/540
See application file for complete search history.

(56) References Cited

U.S. PATENT DOCUMENTS

| 1,961,878 A | 6/1934 | Gilkey .................. 423/210 X |
| 2,203,188 A | 6/1940 | Beer |
| 3,214,364 A | 10/1965 | Van Tuyle et al. |
| 3,421,836 A | 1/1969 | Sundin et al. |
| 3,601,292 A | 8/1971 | Bliss |
| 3,670,425 A | 6/1972 | Benjamin |
| 3,750,556 A | 8/1973 | Duke ........................... 254/159 |
| 3,937,967 A | 2/1976 | Steinitz ....................... 250/435 |
| 3,949,056 A | 4/1976 | Nakshbendi ................. 423/210 |
| 4,045,316 A | 8/1977 | Legan ....................... 204/157.3 |
| 4,238,857 A | 12/1980 | Waters ......................... 2/171.3 |
| 4,309,388 A | 1/1982 | Tenney et al. ................ 422/304 |
| 4,374,571 A | 2/1983 | Hirvela ......................... 239/36 |
| 4,735,010 A | 4/1988 | Grinarml |
| 4,811,159 A | 3/1989 | Foster, Jr. ..................... 361/231 |

(Continued)

FOREIGN PATENT DOCUMENTS

EP    0261987    3/1988

(Continued)

OTHER PUBLICATIONS

Booms Terminator. Game Finder. 2pp. . 2005 [cited in PCT/US2005/004322].

(Continued)

*Primary Examiner* — Sean E Conley
(74) *Attorney, Agent, or Firm* — Holland & Hart

(57) ABSTRACT

Systems and methods for detecting presence of a thing, the thing treated with a descenter, one method including in an area in which it is possible that a thing treated with a descenter is present, using a detector to detect a descenter level in the area, producing a detected descenter level, comparing the detected descenter level to a normal descenter level for the area, determining that the detected descenter level is different from the normal descenter level, said determining indicating the possible presence of a thing treated with a descenter; and using a trained service animal to facilitate such a method.

16 Claims, 7 Drawing Sheets

U.S. PATENT DOCUMENTS

| | | | | |
|---|---|---|---|---|
| 4,863,687 A | 9/1989 | Stevens et al. | | 422/4 |
| 4,867,052 A | 9/1989 | Cipelletti | | 99/451 |
| 4,904,289 A | 2/1990 | Miyakami et al. | | 62/157 |
| 4,941,270 A | 7/1990 | Hoffman | | 34/60 |
| 4,953,674 A | 9/1990 | Landes | | 190/108 |
| 4,990,311 A | 2/1991 | Hirai et al. | | 422/4 |
| 5,087,426 A | 2/1992 | Inoue et al. | | 422/123 |
| 5,152,077 A | 10/1992 | Liang | | |
| 5,185,129 A | 2/1993 | Koutrakis et al. | | 422/88 |
| 5,192,500 A | 3/1993 | Treddenick | | 422/56 |
| 5,303,496 A | 4/1994 | Kowalkowski | | |
| 5,316,182 A | 5/1994 | Lee et al. | | 227/78 |
| 5,342,415 A | 8/1994 | Wasinger et al. | | 8/111 |
| 5,383,236 A | 1/1995 | Sesselmann | | 2/243.1 |
| 5,429,271 A | 7/1995 | Porter | | |
| 5,433,230 A | 7/1995 | Miller | | 134/110 |
| 5,433,919 A | 7/1995 | Baltes | | 422/1 |
| 5,457,054 A | 10/1995 | Geisinger et al. | | |
| 5,468,454 A | 11/1995 | Kim | | 422/121 |
| 5,484,472 A | 1/1996 | Weinberg | | 96/26 |
| 5,514,345 A | 5/1996 | Garbutt et al. | | 422/124 |
| 5,520,893 A | 5/1996 | Kasting, Jr. et al. | | 422/305 |
| 5,539,930 A | 7/1996 | Sesselmann | | 2/243.1 |
| 5,547,476 A | 8/1996 | Siklosi et al. | | 8/142 |
| 5,667,564 A | 9/1997 | Weinberg | | 96/58 |
| 5,681,355 A | 10/1997 | Davis et al. | | 8/137 |
| 5,762,648 A | 6/1998 | Yeazell | | 8/137 |
| 5,766,560 A | 6/1998 | Cole | | 422/186 |
| 5,789,368 A | 8/1998 | You et al. | | 510/297 |
| 5,790,987 A | 8/1998 | Sesselmann | | 2/243.1 |
| 5,795,544 A | 8/1998 | Matz | | |
| 5,829,066 A * | 11/1998 | Aibe | | 4/213 |
| 5,833,740 A | 11/1998 | Brais | | |
| 5,835,840 A | 11/1998 | Goswami | | 422/186.3 |
| 5,891,391 A | 4/1999 | Fore | | 422/5 |
| 5,911,957 A | 6/1999 | Khatchatrian et al. | | 422/186 |
| 5,931,014 A | 8/1999 | Cole | | 62/264 |
| 5,942,438 A | 8/1999 | Antonoplos et al. | | 436/1 |
| 5,983,834 A | 11/1999 | Tai | | 119/448 |
| 6,007,770 A | 12/1999 | Peiper et al. | | 422/22 |
| 6,009,559 A | 1/2000 | Sesselmann | | 2/243.1 |
| 6,074,608 A | 6/2000 | Matz | | 422/83 |
| 6,094,549 A | 7/2000 | Hiraoka et al. | | |
| 6,134,718 A | 10/2000 | Sesselmann | | 2/243.1 |
| 6,134,806 A | 10/2000 | Dhaemers | | 34/404 |
| 6,149,038 A | 11/2000 | Tsai | | 223/86 |
| 6,153,111 A | 11/2000 | Conrad et al. | | 210/741 |
| 6,156,268 A | 12/2000 | Curry et al. | | 422/4 |
| 6,163,098 A | 12/2000 | Taylor et al. | | 310/308 |
| 6,182,671 B1 | 2/2001 | Taylor et al. | | |
| 6,218,189 B1 | 4/2001 | Antonoplos et al. | | 436/1 |
| 6,267,242 B1 | 7/2001 | Nagata et al. | | 206/459.1 |
| 6,284,204 B1 | 9/2001 | Cole et al. | | 422/186 |
| 6,312,645 B1 | 11/2001 | Taylor et al. | | 96/19 |
| 6,336,964 B1 | 1/2002 | Omatsu et al. | | 106/31.44 |
| 6,340,447 B2 | 1/2002 | Johnson | | 422/5 |
| 6,340,497 B2 | 1/2002 | Wilson et al. | | 422/5 |
| 6,355,216 B1 | 3/2002 | Kristiansson et al. | | 422/29 |
| 6,368,867 B1 | 4/2002 | Gibson et al. | | 436/135 |
| 6,379,435 B1 | 4/2002 | Fukunaga et al. | | 96/111 |
| 6,503,547 B1 | 1/2003 | Lima | | 426/231 |
| 6,564,591 B2 | 5/2003 | Noyes et al. | | 68/5 C |
| 6,565,805 B2 | 5/2003 | Khatchatrian et al. | | 422/28 |
| 6,576,190 B1 | 6/2003 | Park | | 422/28 |
| 6,613,277 B1 | 9/2003 | Monagan | | 422/24 |
| 6,630,105 B1 | 10/2003 | O'Neill et al. | | |
| 6,632,407 B1 | 10/2003 | Lau et al. | | 422/186 |
| 6,635,439 B2 | 10/2003 | Morrison et al. | | 435/28 |
| 6,679,419 B1 | 1/2004 | Sarracino | | |
| D486,357 S | 2/2004 | Leba et al. | | D7/605 |
| 6,790,411 B1 | 9/2004 | Read | | 422/28 |
| 6,896,853 B2 | 5/2005 | Lau et al. | | 422/186 |
| 6,967,008 B1 | 11/2005 | Barnes | | |
| 7,117,687 B2 | 10/2006 | Naaman | | 62/259.3 |
| 7,118,608 B2 | 10/2006 | Lovell | | 55/385.1 |
| 7,186,373 B2 | 3/2007 | Centanni | | 422/3 |
| 7,222,634 B2 | 5/2007 | Hess et al. | | 135/93 |
| 7,662,636 B2 | 2/2010 | Maruo et al. | | 436/135 |
| 2002/0030022 A1 | 3/2002 | Bradley | | 210/752 |
| 2002/0071795 A1 | 6/2002 | Jensen | | 422/186.12 |
| 2003/0044308 A1 | 3/2003 | Toth | | 422/5 |
| 2003/0066767 A1 | 4/2003 | Felsenthal | | |
| 2003/0089010 A1 | 5/2003 | Wechter et al. | | |
| 2003/0108460 A1 | 6/2003 | Andreev et al. | | |
| 2003/0111435 A1 | 6/2003 | Chen | | |
| 2004/0002349 A1 | 1/2004 | Yamagishi et al. | | |
| 2004/0047775 A1 | 3/2004 | Lau | | |
| 2004/0096354 A1 | 5/2004 | Nomura et al. | | |
| 2004/0149329 A1 | 8/2004 | Hess et al. | | 135/156 |
| 2004/0163184 A1 | 8/2004 | Waldron et al. | | |
| 2004/0221396 A1 | 11/2004 | Johnson | | |
| 2005/0186108 A1 | 8/2005 | Fields | | |
| 2005/0207951 A1 | 9/2005 | Lee et al. | | |
| 2006/0006122 A1 | 1/2006 | Burns et al. | | |
| 2006/0096331 A1 | 5/2006 | Kim | | 68/5 C |
| 2006/0151896 A1* | 7/2006 | Wang | | 261/89 |
| 2007/0092414 A1 | 4/2007 | Malyon | | 422/186.3 |
| 2007/0166186 A1 | 7/2007 | Stec | | 422/5 |
| 2007/0212253 A1 | 9/2007 | Elrod | | 422/5 |
| 2008/0036594 A1 | 2/2008 | Kates | | 340/541 |
| 2009/0038555 A1* | 2/2009 | Reese | | 119/174 |
| 2009/0139459 A1* | 6/2009 | Habacivch et al. | | 119/420 |
| 2010/0071633 A1 | 3/2010 | Elrod | | 119/712 |
| 2010/0107991 A1 | 5/2010 | Elrod et al. | | 119/712 |
| 2010/0289655 A1 | 11/2010 | Elrod et al. | | |

FOREIGN PATENT DOCUMENTS

| | | |
|---|---|---|
| JP | 06-327749 | 11/1994 |
| JP | 08-168363 A | 7/1996 |
| JP | 09239018 A | 9/1997 |
| JP | 09262141 A | 10/1997 |
| JP | 1109948 A | 1/1999 |
| JP | 11009949 A | 1/1999 |
| JP | 11226106 A | 8/1999 |
| JP | 11226108 A | 8/1999 |
| JP | 2002345937 A | 12/2002 |
| JP | 2003001237 A | 1/2003 |
| JP | 2003024426 A | 1/2003 |
| WO | WO 0151096 | 1/2001 |
| WO | 0177283 A1 | 10/2001 |
| WO | WO 03089017 | 4/2003 |
| WO | WO 2004/067043 | 8/2004 |
| WO | WO 2005077425 A1 | 2/2005 |
| WO | 2005021135 | 3/2005 |

OTHER PUBLICATIONS

U.S. Appl. No. 11/018,620, filed Dec. 21, 2004, Elrod.
Detection of the cyanobaterial hepatoxins microsystins; in toxicology & Applied Pharmacology, McElhiney et al., Dec. 2003 (pp. 219-230).
BOMMS Terminator, Game Finder, May 24, 2002.
Terminator 800, Game Finder, Feb. 13, 2003.
Fehrenbacher, J., Robotic Pollution-Sniffing ECO Dogs, 2 Pages, Feb. 26, 2007.
Machine Language translation for JP 08-1638363A, pub. Jul. 1996.
English language abstract for JP 2002345937 A, pub. Dec. 2002.

* cited by examiner

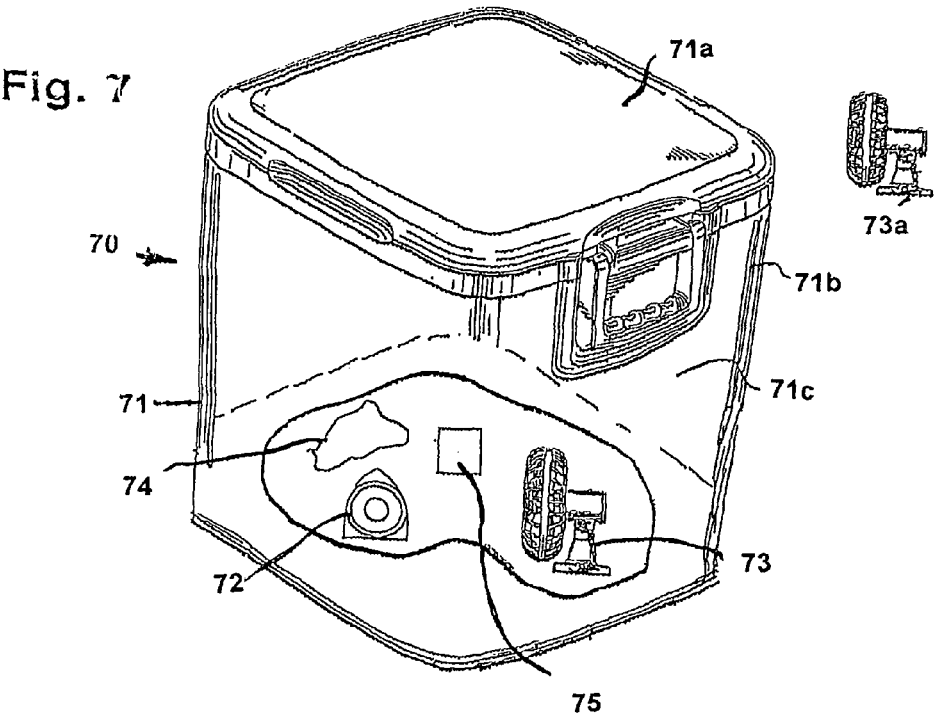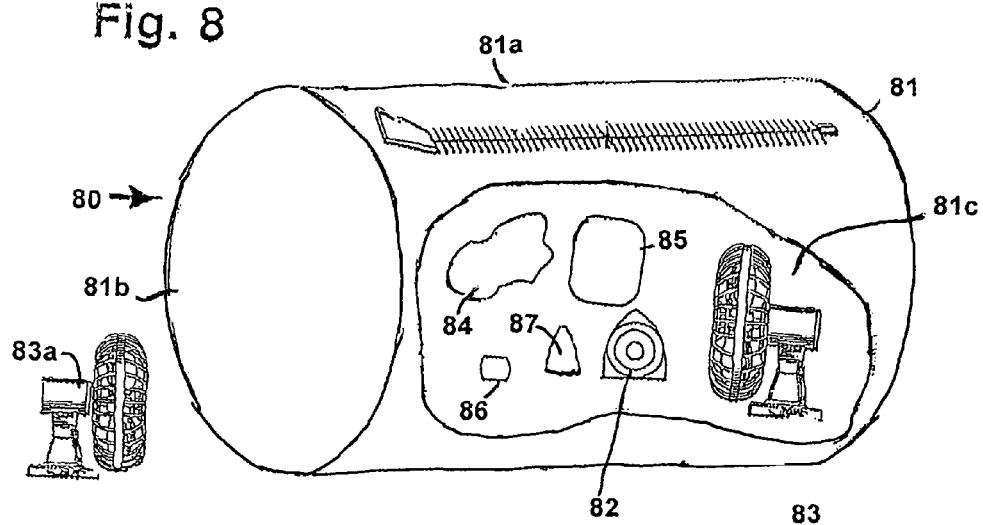

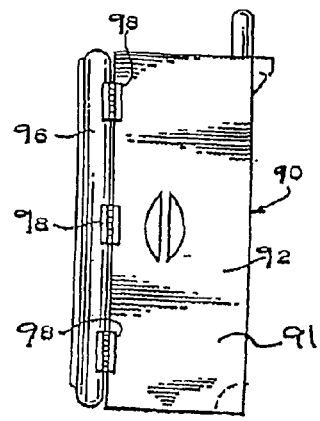
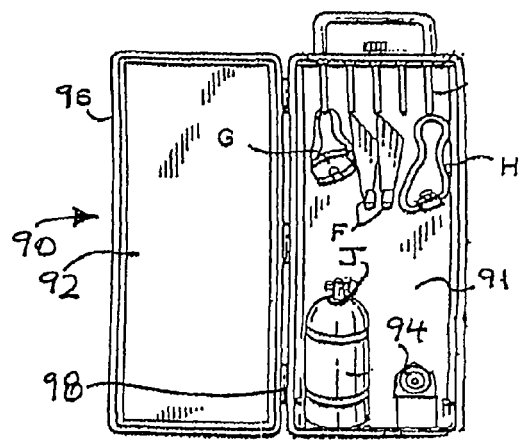
Fig. 9A
Fig. 9B
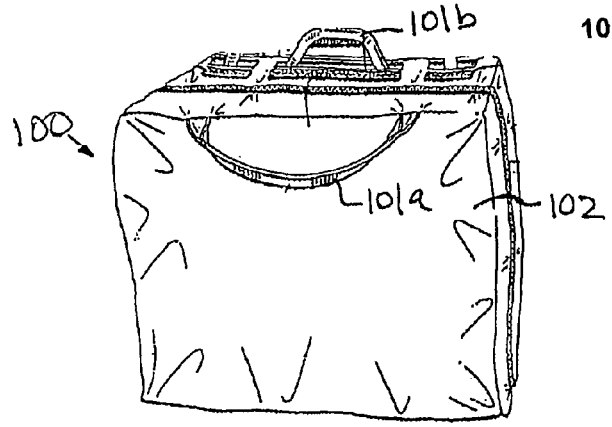
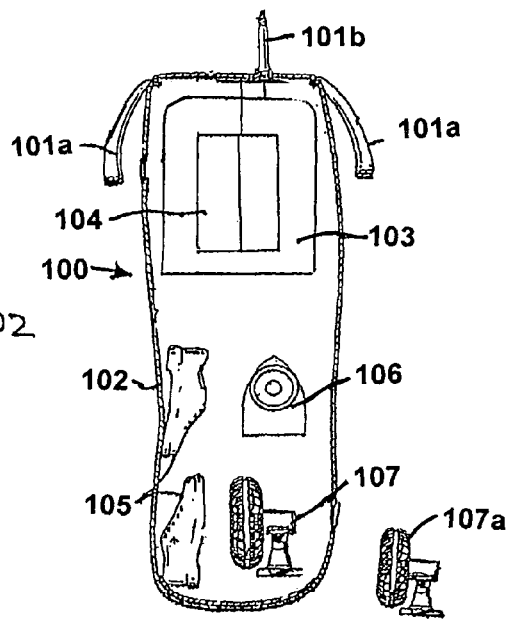
Fig. 10A
Fig. 10B

Fig. 11
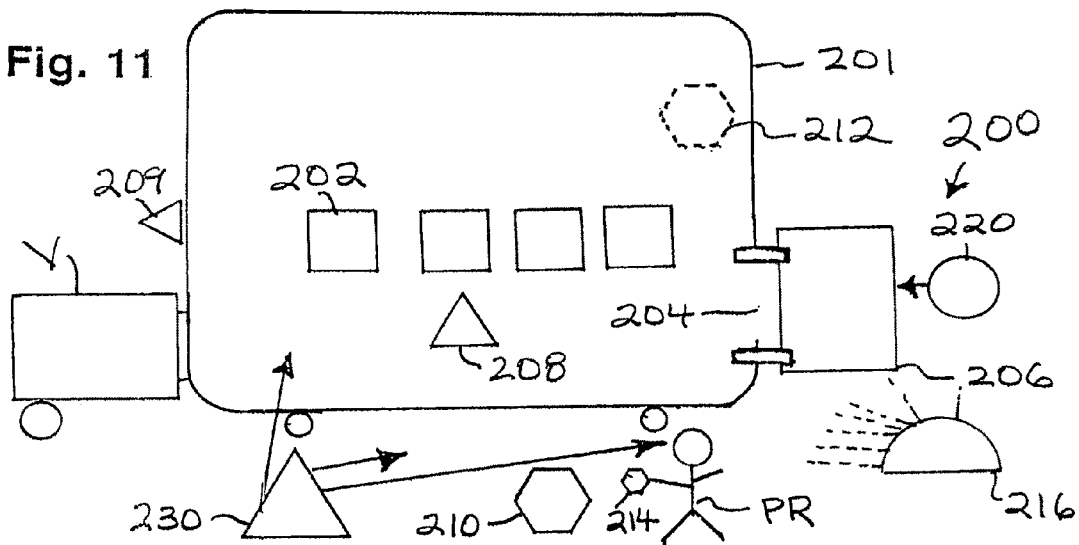
Fig. 12
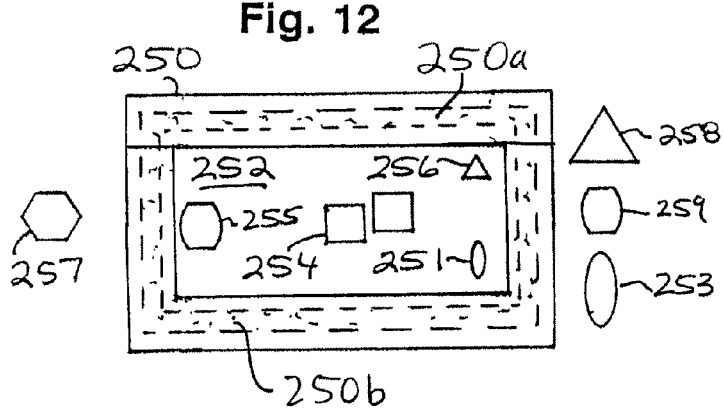
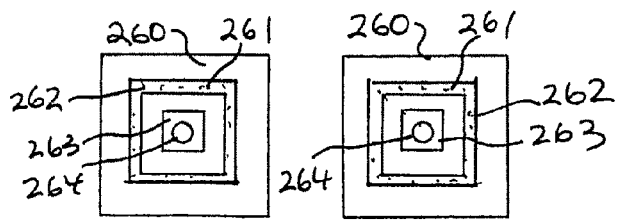
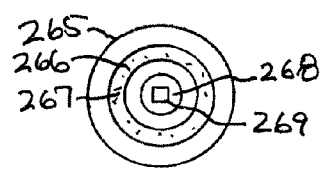
Fig. 12A  Fig. 12B

Fig. 15
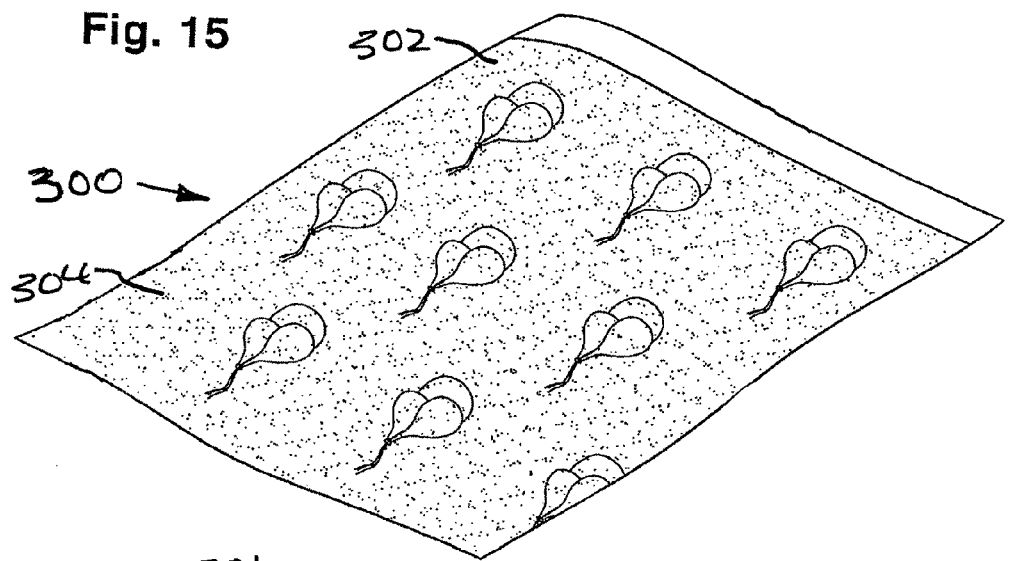
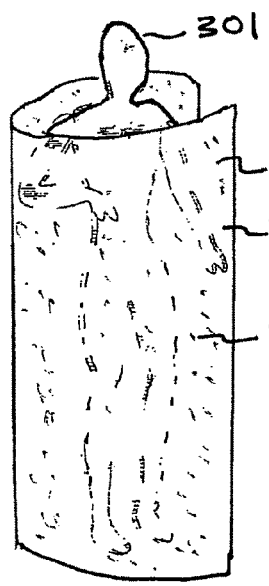
Fig. 16
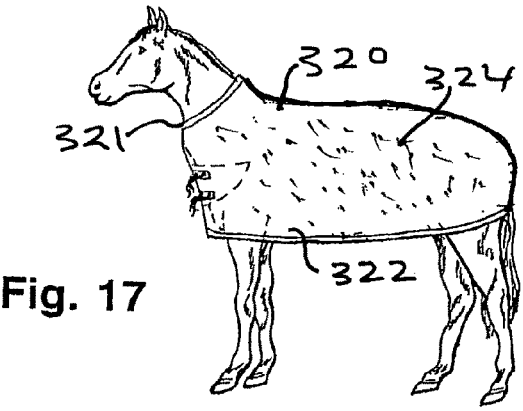
Fig. 17
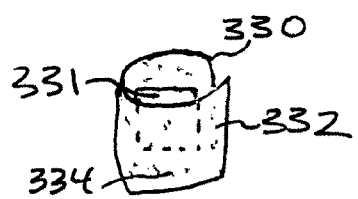
Fig. 18

SYSTEMS AND METHODS FOR DETECTING DESCENTED MATERIAL

CROSS-REFERENCE TO RELATED APPLICATIONS

This application is: a continuation-in-part of U.S. patent application Ser. No. 12/326,240 filed on Dec. 2, 2008 now U.S. Pat. No. 8,187,533; a continuation-in-part of U.S. patent application Ser. No. 11/714,083 filed Mar. 5, 2007 now abandoned; and a continuation-in-part of U.S. patent application Ser. No. 11/018,620 filed Dec. 21, 2004 now U.S. Pat. No. 7,939,015, said applications co-owned with the present invention and incorporated fully herein for all purposes and from which applications the present invention and application claim priority under the Patent Laws.

BACKGROUND OF THE INVENTION

1. Field of the Invention

The present invention is directed, in at least certain embodiments, to systems and methods involving the descenting of transported things: items, materials, and people, including, but not limited to, persons, drugs, explosives, produce, and agricultural products, biological materials (including, but not limited to, bacteria, molds, dander, protein, urine, plasma, sera, viral agents, viruses, yeast, air pollen, blood, spores, protozoa, allergens, semen, radioactive materials, soil, sludge water, ground water, VOCs, biological and/or chemical toxins, cysts, and gaseous agents) and animals; to the transportation of such things with an oxidizing agent generator; and to the detection of things or persons being transported with an operating oxidizing agent generator.

The present invention, in certain aspects, is directed to descenting systems and methods, and in certain particular aspects, to such systems and methods for reducing or eliminating the various odors of contraband through the use of oxidizing or ozone-based descenting products and materials. Additionally, the present invention is directed to systems and methods for the training and detection, by humans and service animals, of the use of such systems and methods for reducing or eliminating the various odors of contraband through the use of ozone-based descenting products. Additionally, the present invention is directed to systems and methods for protecting the health and property of humans and animals exposed to contraband.

The present invention is directed, in certain aspects, to descenting systems and methods; in certain aspects, to such systems and methods for facilitating human/animal encounters and activities; and in other aspects to methods and systems for reducing or eliminating animal and/or human odors that are detectable by animals and/or humans. The invention relates to a method of descenting the clothes and apparatus of sportsmen, both professional, non professional, military personnel, bikers, campers and the like. In certain aspects a method is provided for reducing or removing human scent and any other scent that is not advantageous in an environment from clothing and equipment of hunters and fish odors from fishermen utilizing an oxidizing agent which is ozone and/or a combination of hydroxyl and hydroperoxide ions. More particularly, there is provided a method of reducing or removing human scent and any other scent in a space between a human and an animal that is not advantageous in an environment, including scents emitting from human breath, human bodies, and from clothing and equipment, the methods utilizing an oxidizing agent which is, e.g., ozone and/or a combination of hydroxyl and hydroperoxide ions.

The present inventors have recognized that it can be important to detect the use of a descenting system. For example, service animals, such as narcotic-sniffing canines, have been employed to discern whether individuals are importing contraband into a geographic location. Typically, this determination is done by taking advantage of the inherent acuteness of the canine sense of smell. The importation of such contraband is, obviously, illegal. Nevertheless, in an effort to profit on the "black market," importers (or, more appropriately, smugglers) have taken many steps in an attempt to circumvent the canine sense of smell. One option has been to mask, or cover up, the odor of the contraband, with substances such as coffee grounds. Alternatively, descenting systems and methods, such as that described herein, may be employed. For example, descenting systems may be placed within the presence of the contraband in an effort to reduce or eliminate the odor emanating from such contraband enough to reduce or eliminate the success rate of service animals.

2. Description of Related Art

A variety of descenting (removal of scents) apparatus and methods and of decontamination systems and methods are known, examples of which (and not by way of limitation) are found in U.S. Pat. Nos. 4,309,388; 4,867,052; 4,941,270; 5,087,426; 5,205,999; 5,300,266; 5,433,919; 5,468,454; 5,484,472; 5,514,345; 5,539,930; 5,547,476; 5,566,627; 5,656,242; 5,667,564; 5,681,355; 5,762,648; 5,766,560; 5,788,930; 5,789,368; 5,790,987; 5,827,407; 5,833,740; 5,882,591; 5,911,957; 5,931,014; 5,942,438; 6,007,770; 6,009,559; 6,016,687; 6,027,688; 6,134,806; 6,134,718; 6,149,038; 6,156,268; 6,163,098; 6,228,330; 6,245,241; 6,280,691; 6,284,204; 6,312,507; 6,355,216; 6,379,435; 6,503,547; 6,564,591; 6,565,805; 6,576,190; 6,589,486; 6,630,105; 6,679,419; 6,827,861; 6,984,361; 7,294,318; 7,407,624; 7,510,470; and published U.S. Patent applications 20030044308, 20030101700; 20030143108; 20030152480; 20040022679; 20040258585; 20040262241; 20050051497; 20050186108; 2007166186; 20070034095; 20070101867—all of which are incorporated fully herein for all purposes.

Hunters, wildlife enthusiasts, and wildlife photographers all have an interest in attracting wildlife, such as, but not limited to, deer; and/or an interest in not being detected by animals. Deer rely heavily on their sense of smell to react with their surrounding environment, including to sense danger, interact with other deer and find food. Scents that are not a natural part of the environment will often function as a warning to deer, which may result in the deer being spooked and running from the unnatural scent.

According to Bernier et al in Analytical Chemistry, 2000, volume 72, issue 4, pages 747-756 and references cited therein which are incorporated fully herein by reference, as many as 346 discernible compounds were identified in human skin emanations. The majority of these were carboxylic acids, alcohols and esters, but aldehydes, aromatics, heterocyclics, ketones, sulfides and thio compounds were also identified. Work cited in Bernier has identified over 100 compounds from human breath. Work cited in Bernier identified foot odor as another source of odor. Some of these compounds are the result of bacteria reacting with body emanations, while other compounds directly emanate from humans. Other compounds emanated from humans can include pheromones, deodorants and perfumes as well as the detergents, perfumes, scents, and additives left on human clothes. While it is not known which specific compound or blends of compounds emanating from humans are identified by an animal as human, there is currently no effective way to eliminate or reduce odors from humans and from clothing and equipment enough to reduce the odors to inhibit detection by wildlife or effectively attract wildlife.

Persons interested in preventing detection by deer detecting human odors or interested in attracting deer often use masks, attractants, or cover scents to prevent alerting and spooking the deer. Some commonly used masks are carbon sprays which, in addition to being dangerous to inhale and which can irritate skin, become ineffective once dry. Many of the attractants contain deer urine or estrous, which besides being offensive to the human user, have limited shelf life and are generally ineffective since especially the estrous tend to occur naturally only in certain seasons. Cover scents such as fruit extracts or fragrances last a short time and are often so over-powering that the deer easily identifies the smell as unnatural and runs. The use of descenting soaps and shampoos is messy, time-consuming, often skin irritating, often ineffective and does not address breath odor. Breath descenting using herbs are generally distasteful, and face masks containing carbons or sieves are extremely uncomfortable.

More recently, the use of clothing containing activated carbons and/or clothing containing bacteria killing metals such as silver has gained some popularity. However, activated carbon has a very low capacity for odorants and requires temperatures preferably above 400° C., more preferably above 600° C. to regenerate the carbon. These temperatures are well beyond temperature (100 C to 120 C) that a conventional gas or electric clothes dryer is capable of achieving. Placement of clothing in ovens capable of achieving 400 C plus temperatures needed to regenerate the carbon can damage the fabric of a garment. Silver or other metal-containing clothing requires direct contact of the metal with the bacteria to be effective, which is almost never the case since the clothing would then be so restricting as to be uncomfortable. These types of clothing are also expensive and do not address human odors such as those in human breath, nor do they address any of the odors emanating from the foot or any exposed part of the skin like the head and hands.

It has now been discovered that gaseous ozone effectively kills bacteria and reduces or eliminates odors emanating from humans as well as odors contained in clothing worn by hunters. The advantages of ozone over other known masking and descenting methods include the facts that: ozone is a gas that eliminates odors emanating from a person (e.g., a hunter) and from personal equipment and can eliminate odors in a space between a person and an animal; and ozone is completely natural to the environment and leaves behind a very pleasant clean smell that wildlife and humans readily recognize, e.g. after a lightning rain. Known ozone generators include, for example, electrical discharge, UV light, and combinations thereof. The generator may be battery operated, operated with a car adaptor, and/or may be operated with AC current. The AC current may be supplied directly from an electrical outlet, or may be supplied using a portable generator.

Ozone is well known to treat odorous air, microorganisms, bacteria, mold, smoke, aromatic hydrocarbons, and volatile organic compounds (see for example U.S. Pat. Nos. 1,961, 878; 2,203,188; 3,421,836; 3,750,556; 3,937,967; 3,949,056; 4,045,316; 4,863,687; 4,904,289; 4,990,311; 5,087,426; 5,835,840; 5,983,834; 6,094,549; 6,613,277; 6,632,407; 20020030022; 20060096331; and references cited therein, which are all of which are incorporated fully herein for all purposes); and foreign references EP 261987; WO 200151096; WO 2003089017; WO 2005021135. WO 2005077425 and references cited therein, which are incorporated fully herein for all purposes, teaches the use of ozone to descent hunters clothing and other personal effects to be worn or carried on a hunting trip. In this case, the hunter, the clothing or personal effects are placed in a container, a portable enclosure, or a special descenting closet or room located, e.g., in a lodge or cabin in which the hunter is staying. As soon as the hunter leaves the building and enters a vehicle, or passes a moving vehicle, or begins to sweat, any prior descenting is of little value.

Animals have an acute sense of smell and are capable of recognizing a human scent or any other scent that is not advantageous in that environment at long distances. To avoid such recognition a hunter will attempt to stay down wind of the animal being hunted. Certain known methods used by hunters to trick animals are to mask the human odor utilizing a carbon spray or cover spray scents or an animal scent. Unfortunately the animal scents which are utilized, are obnoxious and linger on the clothing for long periods of time and often do not mask out human scents. Some of the scents utilized include animal urine. A hunter who is camping overnight does not desire the animal scents to be carried over to bedtime, home, car, etc.

There are other drawbacks in utilizing animal scents or any other scents. The scent may attract a predator of the game which the hunter is not hunting for which the hunter may not be prepared to encounter. Containers containing food, beverages, or any other substance emit scents readily recognizable to animals that may not be masked by animal scents or may not be natural to a given environment. Female hikers, campers, hunters, etc. can emit a readily recognizable scent to animals from menstruation that may not be masked by animal scents. Also, the weapon used by the hunter has an odor recognizable by some animals which cannot be disguised with a scent.

Fishermen have the problem of fish odor on their hands and clothes which is difficult to remove. For fishermen camping overnight the fish odor is not only undesirable because of the odor but can also attract animals such as bears which the fishermen is not prepared to meet.

Hunters have prepared their clothing before hand by washing to remove prior scents and/or human odor. The washing materials may also leave an odor. However, out in the field the hunter can sweat and permeate the clothing with a human scent. It would be desirable to deodorize clothing during a hunt or while on a fishing trip.

Ozone has been used, inter alia, for decontaminating smoke from fires; decontaminating buildings; and for decolorizing denim garments. U.S. Pat. No. 5,833,740 discloses an apparatus for sterilizing bottles utilizing ozone. The reference recognizes that ozone in large quantities can be harmful or irritating. Consequently, it was necessary to provide means for decomposing the excess ozone and/or to cause its escape into the atmosphere.

Ozone is a powerful oxidizing agent. Ozone has 150% of the oxidizing potential of chlorine and twice the oxidizing potential of bromine. Ozone has been shown to be much more effective than chlorine with a reaction time up to 10 times faster. Ozone also readily self-destructs into simple diatomic oxygen due to its inherent instability. Ozone oxidizes biological products and kills bacteria.

Catalytic ionization of air using ultraviolet light is known to produce a mixture of ozone-containing hydroxyl and hydroperoxide ions. Ionization devices which are used to eliminate smoke and odors are known in the art to produce hydroxyl and hydroperoxide ions, e.g. those used in automobiles.

Thus, the need exists to develop effective systems and methods which overcome the disadvantages and problems set forth above. The need also exists, recognized by the present inventors, to detect the transport of contraband and to train personnel and animals in such detection.

BRIEF SUMMARY OF THE INVENTION

The present invention, in certain aspects, discloses systems and methods for detecting the transport of things (e.g., material, items, and/or persons) which are being transported with an operating oxidizing agent generator, e.g., but not limited to, such transport done in an effort either to render the transport safer or done in an effort to avoid detection of the materials, things, or persons being transported. In certain aspects, such systems and methods according to the present invention include using a detection system to detect ozone, etc., generated by an oxidizing agent generator being used in the transport of such things. In one particular aspect, a portable handheld oxidant detection device is used to detect the presence of oxidant levels which are above normal.

The present invention discloses, in certain aspects, systems and methods for safely transporting things in a container with a descenter (descenting oxidizing agent) generator. A "descenter generator" can be a unit, apparatus, or device for producing descenter—oxidizing agent descenter, ozone, ozone in various forms, e.g. ozone saturated in organic solvent (see, e.g., Patent Application No. WO2005014113) oxidants, hydroxyl radicals, hydroperoxide radicals, negatively charged metal oxides (see, e.g., U.S. Pat. No. 5,300,366), hydrogen peroxide, encapsulated ozone (see, e.g., U.S. Pat. No. 6,827,861, metastable oxygen (see, e.g., U.S. Pat. No. 6,228,330), activated ozone (see, e.g., Patent Application WO1998019961), peracetic acid (see, e.g., U.S. Pat. No. 5,942,438 and U.S. Application No. 20050057868), chlorine dioxide (see, e.g., U.S. Pat. No. 5,942,438), oxygen and its radicals (see, e.g., U.S. Pat. No. 6,984,361), thixotropic gels (see, e.g., U.S. Pat. No. 6,455,751), singlet oxygen via ozone or via hydrogen peroxide (see, e.g., U.S. Pat. No. 6,630,105), UV light at 254 nm which disinfects but does not produce ozone (see, e.g., U.S. Pat. No. 6,630,105), UV light at 185 nm which produces ozone (see, e.g., U.S. Application No. 20030086818), ozone plus hydrogen peroxide (see, e.g., U.S. Pat. No. 7,407,624), hypochlorite (see, e.g., U.S. Application No. 20050057868), hydrogen peroxide (see, e.g., U.S. Pat. No. 6,245,241) and chlorite (see, e.g., U.S. Application No. 20070034095) (collectively referred to as "descenters") and it can be inside and/or outside the container (and, in one aspect, in at least one layer or space between an inner chamber and the outside of the container). In one aspect, such a generator produces descenter, e.g. ozone or ozone etc. around a container to provide a protective zone around the container.

In certain particular aspects of the present invention, a container is dehydrated (totally, partially, exterior only, interior only, both exterior and interior, and/or a layer or space within a container is dehydrated) to amplify the effect of ozone, etc., applied to a container with an oxidizing agent generator. In one aspect, the container is dehydrated (e.g., with a dehydrator apparatus which, in one aspect, may be a portable apparatus); with an electronic dehydrator; and/or with water-absorbent material (e.g. silica, drirerite, ethylene glycol, diethylene glycol, triethylene glycol and the like). In other particular aspects the effects of any system, apparatus, device or method according to the present invention are enhanced by dehydrating things, containers, vehicles and/or persons.

In certain particular aspects, the present invention discloses methods for reducing the injurious effects of contraband or of dangerous materials or substances on persons (or animals) encountering them. In one particular aspect, the injurious effects of a substance or material contacting, taken in, or inhaled by a person (or animal) are reduced or eliminated by directing descenter, e.g. ozone etc., to the person (or animal), which contacts, is taken in by, or is inhaled by the person. The inhaled ozone can take effect in the nose, mouth, nasal passages, lungs, respiratory tract, and blood of the person (or animal).

In another particular aspect, the injurious effects of a substance or material contacting the skin of a person (or animal) are reduced or eliminated by directing descanter, e.g. ozone etc., to the skin of the person (or animal). In one aspect, this is done until the person feels some relief. For example, a person who has come into skin contact with poison ivy can direct descanter to the skin and reduce or neutralize the effects of the poison ivy onto the skin.

In certain aspects, systems and methods according to the present invention provide for the application of descenter, e.g., ozone etc. to an area, space, or zone in which narcotic and/or toxic substances are detected to reduce or eliminate injurious effects of such substances on persons, or animals nearby. In one particular aspect, the ozone etc. is applied via air duct(s).

In certain aspects, systems and methods are provided according to the present invention which include the use of material (cloth, fabric, gauze, blanket, tarp, canvas, clothing, paper, cardboard, etc. made from any known fabric or cloth material, including, but not limited to natural fabrics, synthetic fibers and fabrics, plastic cloth material, plastic fabric material, and plastic flexible material) which has descenter, e.g. ozone etc., bound to it or which has absorbed ozone etc. A thing (to include an item, animal, or person) is wrapped, in whole or in part, in at least one layer of the material according to the present invention to prevent or render more difficult detection of the thing by humans or by animals; or to reduce or eliminate the injurious effects (e.g., but not limited to, burns, rashes, bacteria, gangrene, irritation) of toxic materials or substances on the item, thing, animal, or person to reduce or eliminate the injurious effects of additional toxic materials or substances from contacting the person or animal having material wrapped or applied onto them. Such wrapping may also be done according to the present invention to reduce body odor; to reduce airborne odors from a person or animal; or to wrap food.

In certain aspects, optionally, descenter bound to material changes the color of the material when descenter is bound to the material and/or changes color when descenter is reduced from the material. This allows, for example, a visual detection by a person and/or by an instrument or by a detector that the material has descenter within or on the material so that, for example, it can be determined when the material needs to be recharged with descenter or the material needs to be removed and replaced with new material.

The present invention, in certain aspects, provides systems and methods for reducing or eliminating the various odors of contraband through the use of ozone etc. or oxidant-based descenting products.

In certain aspects, the present invention discloses systems and methods for the training and detection, by service animals and their handlers, of the use of such systems and methods for reducing or eliminating the various odors of contraband through the use of descenting products or materials.

In certain aspects, the present invention discloses a method in which descenter, e.g. ozone etc., is unexpectedly used to conceal contraband from humans, service animals and their handlers, the animals having been trained to detect small amounts of odor from contraband that humans cannot generally detect. Additionally, the present invention discloses a method in which a descenting system is used to train contraband-detecting service animals to determine if a system, such as one according to the present invention, is being or has been used in an attempt to eliminate the scent of the contraband. Additionally, the present invention discloses methods in which the detection of descenter, e.g. ozone etc., to conceal contraband can be detected by the use of humans, service animals, handlers of service animals, and by detecting devices.

The present invention, in certain aspects, discloses a method in which once the detection of descenter, e.g. ozone etc., to conceal contraband is recognized, additional descenter, e.g. ozone etc., is applied to prevent adverse health effects to humans, animals, as well as physical damage to the property and to an area in which the contraband is located.

The present invention, in certain aspects, discloses systems and methods which use gaseous descenter, e.g. ozone, to kill bacteria and reduce or eliminate odors emanating from humans, e.g. in breath or from skin, as well as odors in clothing worn by a person that are volatilized into the air space between the human and the wildlife to prevent wildlife from detecting the presence of humans and/or to enhance encounters with and the attraction of wildlife. One embodiment is directed to wearing or carrying a portable generator while walking, waiting for, or engaging in attracting wildlife. Another embodiment is directed to wearing or carrying a portable generator while engaging in an activity, e.g. walking, waiting for wildlife, or engaging in preventing wildlife from detecting the presence of humans. Another embodiment is directed to clothing incorporating or combined with descenter, e.g. ozone etc., directing apparatus or devices. Yet another embodiment is directed to the treatment of clothing—e.g. directly with descenter, e.g. ozone etc., prior to or while being worn—to enhance the attraction of wildlife. Yet another embodiment is directed to the use of gaseous descenter in or around a tent, site, or blind to reduce or eliminate odors to enhance the attraction of wildlife, e.g. for hunters, wildlife enthusiasts and wildlife photographers. Yet another embodiment is directed to the use of gaseous descenter in or around a tent, site, or blind to reduce or eliminate odors to prevent the detection of humans by wildlife, e.g., for hunters, wildlife enthusiasts, and wildlife photographers.

The present invention discloses a method for deodorizing the clothing and apparatus of person, sportsmen, professional or non professional. More particularly, there are provided methods for reducing or eliminating human scent or any other foreign scent from clothing etc.; and there are provided methods for removing human scent or any other foreign scent (collectively "foreign scents") from items and/or clothing, e.g. clothing used by hunters before or during a hunt—through the use of descenter, e.g. ozone or hydroxyl and hydroperoxide ions produced by ionization, in a manner that would not cause irritation or injury to the user or equipment. Also, there is provided a method for removing fish odor from fishermen and their clothing and equipment while in the field including lures, tackle boxes and containers. One principal objective of the invention is the provision of a method for effectively removing human scent from clothing used by sportsmen.

The present invention discloses, in certain aspects, a method for military personnel to escape detection by other humans or by scent animals (e.g., scent dogs). In certain particular aspects the present invention provides methods for reducing or eliminating human or any other foreign scent from items, e.g. from clothing and equipment, used by military personnel desiring to evade detection or capture—through the use of descenter, e.g., ozone etc. and/or ozone with hydroxyl and hydroperoxide ions produced by ionization, in a manner that would not cause irritation or injury to the user or equipment.

It is another object of the invention to use descenter to deodorize fish odor on fishermen.

It is yet another object of the invention to de-scent or deodorize sportsmen while out in the field by the use of descenter, e.g. ozone or hydroxyl and hydroperoxide ions.

Yet another object of the invention is to provide a method of deodorizing clothing with descenter, e.g. ozone etc., so that it will not cause irritation or harm.

It is a further object of the invention to provide descenter, e.g. ozone etc., in a compressed or generated form in a hand held container for application in the field by sportsmen.

For safety reasons, government regulations have recommended, and sometimes regulated, the amount of ozone to which a human is to be exposed. For example, OSHA requires that employee permissible exposure limit (PEL) as an eight hour time-weighted average value of 0.1 ppm ozone in air. The OSHA short term exposure limit (STEL) is 0.3 ppm over a 15 minute period, not to be repeated more than two times in an eight hour period. Prolonged exposure of humans has produced no apparent ill effects at 0.2 ppm. In a variety of embodiments of the present invention, a human being is exposed to ozone generated by an ozone generator. In any such embodiments the human being may be limited to exposure to ozone in a concentration of 0.2 parts per million (or less). In any such embodiment, in certain aspects, in which the human being is to be exposed to ozone for a time period of up to about 8 hours (about 8 hours or less), the ozone concentration is limited to 0.1 parts per million (or less). In any such embodiment, a desired level of ozone concentration to which the human being is exposed is maintained in a space of a desired size around the human being, e.g., in certain aspects, a desired level of ozone is maintained within about a 6 foot radius of the human being (and, in one aspect, at an ozone concentration level of 0.2 ppm or less and, in another aspect, at an ozone concentration of 0.1 ppm or less).

In certain aspects the descenting material generators used in systems and methods according to the present invention are light weight and portable, and powered by battery means, solar means, hand crank means (e.g., but not limited to, for instances in which one carries small amounts of contraband on one's person or in a small container or suitcase) or other generating means. When the contraband is in a larger container, such as building, a room, truck container or automobile, or when larger amounts of contraband are involved, it is preferable to have the same features. Nevertheless, even when large amounts of contraband are involved, it is still preferable to use the smallest, low weight generators possible that will effectively descent the contraband, as these may be better hidden from visual detection. However, generators weighing up to about 8 lbs. and more may still be used.

One advantage of including at least a small fan (and such can be included with any system or method according to the present invention) is that the descenter, e.g. ozone etc., can be dispersed over a large area more readily. However, it is not necessary that a fan be included in the descenting material generator. For example, when treating a larger area like a truck container, especially if the container is full of contraband, or contains a smaller amount of contraband hidden within a larger amount of legal cargo, a generator having a fan or fan blower is preferred, but not required. If a fan or fan blower is used, a fan can be used which makes minimum noise, especially beyond about a ten foot radius of fan operation so as not to be audibly detected by a human, handler or service animal.

Certain descenting material generators are capable of producing approximately 15-5000 mg and more, per hour. For safety consideration, it is desired that the contraband is exposed to a constant concentration of 0.1 ppm of descenter, e.g. ozone, or less in such a concentration over an 8 hour time period or less, especially when the contraband is a human or animal, however, exposures of contraband to larger concentrations, e.g., up to 0.2 ppm ozone and more, may be desirable to effectively mask contraband having high odors, such as marijuana and fruits. A preferred descenting material generator is one which can maintain about 0.1 ppm or less total ambient concentration of ozone over an area of approximately a six foot radius of the contraband.

In certain aspects, the present invention discloses a method for reducing contraband scent in a space between the contraband and the service animal, the methods including generating descenting material with a material descenting generator, introducing the descenting material into a space between a human being and the service animal, the space containing foreign scent (i.e., odor emanating from the contraband), and reducing the foreign scent in the space with the descenting material. In certain embodiments, the descenting material is ozone and the method further includes exposing the contraband to a time-weighted average value of 0.1 ppm of ozone in ambient air or less over an area within a radius of six feet of the contraband; exposing the contraband to a time-weighted value of 0.2 ppm or ozone in ambient air or less; or exposing the contraband over a time period of eight hours or less to a time-weighted value of 0.1 ppm of ozone in ambient air or less.

In other aspects, the present invention discloses a method for reducing foreign scent in a space between contraband and the service animal, the methods including producing descenting material with a material descenting generator with directional apparatus, directing said descenting material in a desired direction into the space, the directional apparatus including at least one director in communication with the generator for receiving produced descenting material from the generator and for directing said descenting material into the space, and reducing the foreign scent (i.e., the odor emanating from the contraband) in the space with the descenting material. In certain embodiments, the descenting material is ozone and the method further includes exposing the contraband to a time-weighted average value of 0.1 ppm of ozone in ambient air or less over an area within a radius of six feet of the contraband; exposing the contraband to a time-weighted value of 0.2 ppm or ozone in ambient air or less; or exposing the contraband over a time period of eight hours or less to a time-weighted value of 0.1 ppm of ozone in ambient air or less.

For humans that are avoiding an encounter with a service animal, e.g., those attempting to conceal only small amounts of contraband past a handler or law enforcement officer, a small battery-powered descenting material generator, such as the BIOZONE Model 50 Personal Air Purifier, can be used. For persons attempting to conceal contraband for an extended period, e.g., an hour or more, a larger ozone generator, such as the BIOZONE SCIENTIFIC TRAVELAIRE generator, the OMZ-200 generator from Ozone Solutions or the Ozonics HR-100 ozonator from Ozonics, can be used. For those engaging in concealing larger amounts of contraband, descenting material generator, such as the Ozonics HR-100 ozonator from Ozonics, can be used. Alternatively, the OZONE SOLUTIONS Model MZ-450 or the OZONE SOLUTIONS OMZ-3400 can be used. The MZ-450 and OMZ-3400 are primarily suited for 110V A/C operation, but can alternatively be operated with for four or more hours on a single battery charge. For even higher amounts of ozone output, descenting material generators currently sold by Eco-Quest International of Greeneville, Tenn., which also sells generators of hydroxyl and hydroperoxide ions, may be preferred.

In certain embodiments according to the present invention, material or clothing is treated with descenter, e.g. ozone etc., so that descenter, e.g. ozone etc., is retained on the material, e.g. for several hours and, in certain aspects, for up to hours, and in other embodiments for more than 24 hours. Retained descenter continues to descent scents (and, in some aspects, kill or reduce harmful bacteria and/or toxins), which come in contact with the descenter. A variety of material and cloths, including, but not limited to knits, gauze, fleeces, cotton cloth, cotton blended cloth, fibrous cloth, and rough cloths, have retained ozone. In other embodiments treatment with ozone temporarily changes the color of colored material or cloth and then, after some time period (e.g., when the material or cloth is contacted with odors, bacteria, or toxins), the cloth or material returns to its original color. This color change indicates that an item of material or clothing has been treated with descenter, e.g. ozone etc.; that it is retaining some descenter thereon; and the change back to an original color indicates descenter is reduced and/or is no longer being retained on the clothing to reduce or eliminate odors, bacteria and/or toxins coming in contact with the cloth or material. "Color" refers to any color (e.g., but not limited to, white, red, green, blue, yellow, orange, violet, black, purple, brown, etc.). Such a change in color can be permanent, or preferably is reversible when recontacted with additional oxidant (e.g. ozone).

Accordingly, the present invention includes features and advantages which are believed to enable it to advance descenting technology. Characteristics and advantages of the present invention described above and additional features and benefits will be readily apparent to those skilled in the art upon consideration of the following detailed description of preferred embodiments and referring to the accompanying drawings.

What follows are some of, but not all, the objects of this invention. In addition to the specific objects stated below for at least certain preferred embodiments of the invention, there are other objects and purposes which will be readily apparent to one of skill in this art who has the benefit of this invention's teachings and disclosures. It is, therefore, an object of at least certain preferred embodiments of the present invention to provide:

New, useful unique, efficient, nonobvious systems and methods for detecting the transport of certain material, things, animals or persons and, in one aspect, detecting if such transport is being done or has been done with descenter, e.g. ozone etc., from an oxidizing agent generator;

Such systems and methods in which a transported item, thing, material, or person or a container for such is dehydrated;

New, useful unique, efficient, nonobvious systems and methods for detecting transportation of an item, thing, material or person being transported with an operating oxidizing agent generator;

New, useful, unique, efficient, nonobvious methods and systems for enhancing encounters with or the attraction of animals (including, but not limited to, human beings);

Such systems and methods including the treatment of clothing and other items with descenter, e.g. ozone etc.;

Such systems and methods including wearing descenter directing apparatuses;

New useful, unique, efficient, nonobvious systems and methods for reducing foreign scent in a space between a human being and an animal;

New, useful, unique, efficient, nonobvious methods and systems for substantially reducing or eliminating the odor or scent (collectively "odor") of contraband;

New useful, unique, efficient, nonobvious systems and methods for teaching service animals and their handlers to detect the use of such systems and methods on contraband;

New useful, unique, efficient, nonobvious systems and methods to protect the health and property of humans and animals exposed to toxins and/or contraband;

New useful, unique, efficient, nonobvious systems and methods to protect the health and property of humans and animals exposed to contraband contained in water and soil; and New useful, unique, efficient, nonobvious systems and methods to protect the health and property of humans and animals exposed to airborne toxins and/or contraband.

Certain embodiments of this invention are not limited to any particular individual feature disclosed here, but include combinations of them distinguished from the prior art in their structures, functions, and/or results achieved. Features of the invention have been broadly described so that the detailed descriptions that follow may be better understood, and in order that the contributions of this invention to the arts may be better appreciated. There are, of course, additional aspects of the invention described below and which may be included in the subject matter of the claims to this invention. Those skilled in the art who have the benefit of this invention, its teachings, and suggestions will appreciate that the conceptions of this disclosure may be used as a creative basis for designing other structures, methods and systems for carrying out and practicing the present invention. The claims of this invention are to be read to include any legally equivalent devices or methods which do not depart from the spirit and scope of the present invention.

The present invention recognizes and addresses the previously-mentioned problems and long-felt needs and provides a solution to those problems and a satisfactory meeting of those needs in its various possible embodiments and equivalents thereof. To one of skill in this art who has the benefits of this invention's realizations, teachings, disclosures, and suggestions, other purposes and advantages will be appreciated from the following description of certain preferred embodiments, given for the purpose of disclosure, when taken in conjunction with the accompanying drawings. The detail in these descriptions is not intended to thwart this patent's object to claim this invention no matter how others may later disguise it by variations in form, changes, or additions of further improvements.

The Abstract that is part hereof is to enable the U.S. Patent and Trademark Office and the public generally, and scientists, engineers, researchers, and practitioners in the art who are not familiar with patent terms or legal terms of phraseology to determine quickly from a cursory inspection or review the nature and general area of the disclosure of this invention. The Abstract is neither intended to define the invention, which is done by the claims, nor is it intended to be limiting of the scope of the invention in any way.

It will be understood that the various embodiments of the present invention may include one, some, or all of the disclosed, described, and/or enumerated improvements and/or technical advantages and/or elements in claims to this invention.

BRIEF DESCRIPTION OF THE SEVERAL VIEWS OF THE DRAWING

A more particular description of embodiments of the invention briefly summarized above may be had by references to the embodiments which are shown in the drawings which form a part of this specification. These drawings illustrate embodiments preferred at the time of filing for this patent and are not to be used to improperly limit the scope of the invention which may have other equally effective or legally equivalent embodiments.

FIG. 7 is a perspective view, partially cutaway, of a system useful in methods according to the present invention.

FIG. 8 is a perspective view, partially cutaway, of a system useful in methods according to the present invention.

FIG. 9A is a side view of the system according to the present invention.

FIG. 9B is an open front view of the system of FIG. 9A.

FIG. 10A is a front perspective view of a system according to the present invention.

FIG. 10B is an unfolded cross-section view of the system of FIG. 10A.

FIG. 11 is a schematic view of a system according to the present invention.

FIG. 12 is a schematic view of a container according to the present invention.

FIG. 12A is a front cross-section view of a container according to the present invention.

FIG. 12B is a top cross-section view of the container of FIG. 12A.

FIG. 12C is a cross-section view of a container according to the present invention.

FIG. 15 is a perspective view of a blanket according to the present invention.

FIG. 16 is a perspective view of use of a blanket according to the present invention with a person.

FIG. 17 is a perspective view of use of a blanket according to the present invention with an animal.

FIG. 18 is a perspective view of use of a wrap according to the present invention with a thing.

Figure 1:
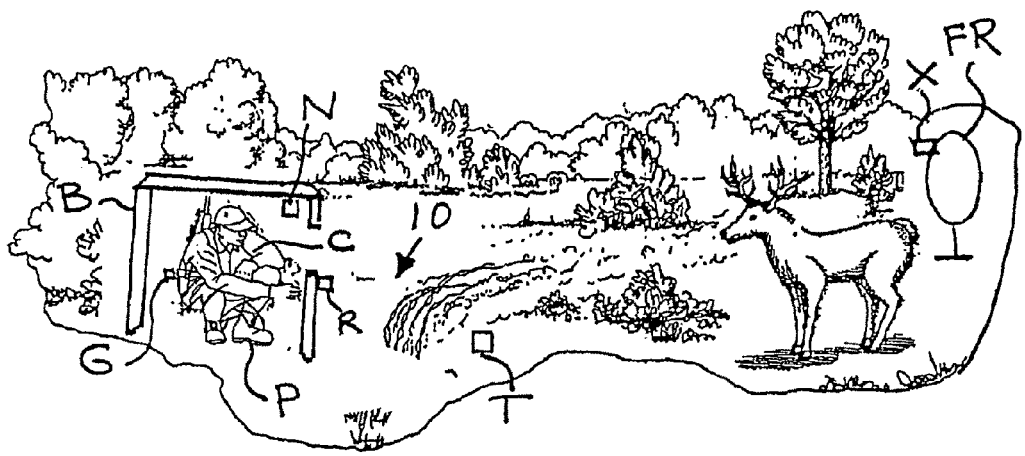
FIG. 1 is a perspective view showing use of systems according to the present invention.

Certain embodiments of the invention are shown in the above-identified figures and described in detail below. Various aspects and features of embodiments of the invention are described below and some are set out in the dependent claims. Any combination of aspects and/or features described below or shown in the dependent claims can be used except where such aspects and/or features are mutually exclusive. It should be understood that the appended drawings and description herein are of certain embodiments and are not intended to limit the invention or the appended claims. On the contrary, the intention is to cover all modifications, equivalents and alternatives falling within the spirit and scope of the invention as defined by the appended claims. In showing and describing these embodiments, like or identical reference numerals are used to identify common or similar elements. The figures are not necessarily to scale and certain features and certain views of the figures may be shown exaggerated in scale or in schematic in the interest of clarity and conciseness.

As used herein and throughout all the various portions (and headings) of this patent, the terms "invention", "present invention" and variations thereof mean one or more embodiments, and are not intended to mean the claimed invention of any particular appended claim(s) or all of the appended claims. Accordingly, the subject or topic of each such reference is not automatically or necessarily part of, or required by, any particular claim(s) merely because of such reference. So long as they are not mutually exclusive or contradictory any aspect or feature or combination of aspects or features of any embodiment disclosed herein may be used in any other embodiment disclosed herein.

DETAILED DESCRIPTION OF THE INVENTION

"Person" as used herein includes, but is not limited to, traveler, animal handler, medical patient, government employee, government employee at a border, government employee at a customs office, policeman, military personnel, military personnel seeking to evade others and/or avoid capture, inspector, law enforcement officer, and hunters.

"Hunter" is defined as including hunters of wild game and other animals and also includes nature enthusiasts, trappers, hikers, fishermen and fisherwomen, backpackers, and photographers; and "hunt" or "hunting" is defined as including the searching for and the hunting of wild game and other animals for the purposes of encountering, attracting, avoiding, escaping from, photographing, avoiding detection by, capturing, killing and/or observing them.

"Animal" as used herein includes, but is not limited to, any small or large game animal including deer, elk, sheep, pig, moose, cow, bull, human being, steer, dog, cat, caribou, bird, rabbit, elephant, mountain lions, bear and fish, and combinations thereof and, in certain aspects, "animal" includes human beings. For example, a human may desire to prevent the detection of human body odors or odors resulting from the illegal transport of humans or from the human consumption of various foods and/or spices (e.g., pepper or curry) and/or beverages by the human himself or herself or by another human.

"Blind" as used herein includes any natural or man-made place of observing, hiding and/or protecting a person including, but not limited to, a tent, shack, tree stand, shrubs, cut limbs, rocks, place for protection from natural elements, and combinations thereof.

"Handler" is a police officer, narcotics officer, game warden, customs officer, border patrol agent, security officer, animal trainer, law enforcement officer, civilian and the like, that uses a service animal to detect material, things, and/or contraband.

"Service animal" is any animal, such as a human, dog, cat, bird, pig, fish, dolphin and the like, that is capable of being trained to detect contraband.

"Contraband" is any substance that is illegal to possess or transport under the law or regulations of any sovereign country or entity, and which, in some cases, is the subject of or maintains a black market, such as illegal drugs, marijuana, cocaine, heroin, amphetamines, apples, oranges, pineapples, bananas, explosives, plastiques, radioactive materials and wastes, toxins (e.g. ricin), gun powder, exotic birds, reptiles, fish, mammals, humans and paper currency (both genuine and counterfeit). Contraband also includes toxins and biological agents/weapons such as: viruses, germs, bacteria, allergens, pathogens, cyanide (e.g. HCN, KCN), phosgene, tear gas, mustard gas, anthrax, botulinum toxin, aflatoxin, *Salmonella Typhimurium, Ascaris suum, B. anthracis*, ricin, plague, smallpox and more such as is described in the Department of Health and Human Services Centers for Disease Control and Prevention Emerging Infectious Diseases Journal, "Potential Biological Weapons Threats", located at http://www.cdc.gov/ncidod/EID/vol5no4/kortepeter.htm.

"Descenting material generator" includes generators that produce descenter, e.g., ozone etc. material as a gas, a fine mist, a spray with solids, or some combination thereof that is capable of descenting human scents, and/or of killing or reducing germs and/or bacteria, or descenting and/or masking and/or reacting with contraband; the materials including, but not limited to, oxidants, ozone, hydroxyl radicals, hydroperoxides, and other known descenting materials; with or without an operating integrated fan. A "mist" produced by such a generator is a mist of descenting material and a liquid, e.g. water or organic-solvent material (e.g. alcohols like methanol or ethanol or isopropanol or glycol ether, e.g. ethylene glycol methyl ether and ethylene glycol dimethylether) that is capable of solubilizing descenting material.

FIG. 11 shows a system 200 according to the present invention which includes an enclosure 201 which, in certain aspects is a container, cab, enclosed trailer or storage part of a vehicle V. Within the enclosure 201 is at least one or a plurality of things 202 being transported in the enclosure 201 (e.g., but not limited to material, items, animals and/or persons).

In one aspect, a detector 210 (for detecting descenter, e.g. ozone etc.) is used to detect the presence of an abnormally high level of descenter, e.g., ozone etc., in and/or around the enclosure 201 (generated, e.g. by an on-board generator 208 and/or 209) which can indicate efforts to transport the thing(s) 202 in a manner to inhibit or prevent the detection of the thing(s) 202 by an animal trained to smell such things. Alternatively, or in addition to the use of the detector 210, a person PR may, according to the present invention, use a handheld or portable detector 214 for detecting the presence of descenter, e.g., ozone, etc. Optionally, a detector 212 is used within the enclosure 201 to detect a level of ozone etc. or an abnormally high level of ozone, etc.

The detector 210 may have a probe or tube to allow for poking the probe or tube into various depths of the container to detect the presence of abnormally high levels of descenter (e.g. ozone, etc.). The detector may optionally also have an input at, in, or very near the detector 210 to also measure ambient descenter (e.g. ozone, etc.) levels so that a difference of ambient level versus an abnormally higher level can be better compared and detected.

In order to nullify or ameliorate injurious effects of exposure to the thing(s) 202 (and/or to air carrying air-borne particles, pieces, or parts of the thing(s) 202), an optional generator 230 is provided, according to the present invention, to produce additional oxidizing agent and provide it to the interior of the enclosure 201 and/or to personnel either within the enclosure 201 or on the outside thereof. Optionally, the generator 208 is provided within the enclosure 201 to generate descenter, e.g. ozone, etc., within the container and/or optionally in at least one zone between the inside of the container and the outside of the container.

To facilitate detection of an abnormally high level of descenter, e.g., ozone, etc., a door, hatch, or closure 206 is opened so that air can pass freely through an opening 204 to ventilate the enclosure 201 for accurate sensing and readings. To further facilitate air flow, a fan 220 directs air to circulate into and out of the enclosure 201.

A control system 216 [e.g. but not limited to a PLC, desktop computer(s), and/or laptop computer(s) with appropriate screen(s), printer(s), etc.] is in communication with each detector, generator, and fan to receive signals indicative of ozone levels, provide information to an operator, and provide automatic and/or manual control of each detector, generator, and fan.

It is within the scope of the present invention to provide an enclosure which optionally contains at least one zone, space, layer or area between the inside and outside of the container where descenter (e.g. ozone, etc.) is contained. In this way, the contents of the container or a thing being transported is less exposed to the oxidant, but still odor from the thing is adequately reduced so escape from the container via the walls (top, bottom and sides) of the container is reduced. Further, optionally at least part of the container is made of descenter absorbing material, that optionally has the ability to change color to indicate when descenter is present and/or reduce and needing additional descenter to be effective against odor, germs, bacteria and other effects on the container and contents of the container.

FIG. 12 shows a container 250 according to the present invention which has one or more things 254 contained in an interior 252 of the container 250. A generator 256 provides descenter, e.g., ozone etc. within the container 250 around the thing(s) 254. Optionally (or instead of the generator 256), another generator 258 is provided exterior to the container 250 for generating descenter, e.g., ozone etc. (e.g. for diminishing the effects of airborne parts of the things 254 and/or for the protection of personnel near the container 250). Optionally, and as is true for any enclosure or container according to the present invention, the container 250 may have a space 250a which encompasses the container's interior and which has therein descenter 250b, e.g., ozone or ozone etc., which is prevented from reacting with the contents of the container.

In one aspect, a dehydration apparatus 255 is provided within the container 250 to dehydrate the interior 252 thereby enhancing the effects of the descenter, e.g. ozone, etc. provided by the generator 256 (and/or the generator 258). Optionally (or instead of the apparatus 255), a dehydration apparatus 259 is provided outside the container 250 for the same purposes. In any of the spaces, zones, or layers of any enclosure described herein, such a space, zone, or layer may be dehydrated according to the present invention.

Ventilation can be provided for the container 250 as it is for the enclosure 201 (and ventilation can be provided for any space, zone, area, or layer of any enclosure or container according to the present invention).

Optionally, a cooling system 251 (inside) and/or a cooling system 253 (outside) are provided to cool the container 250 and/or its contents (and such cooling can be provided for any space, zone, area, or layer of any enclosure or container according to the present invention). Cooling diminishes perspiration and odor vaporization.

FIGS. 12A and 12B show a container 260 according to the present invention which is a cube. A thing 264 is contained in a cube-shaped chamber 263 within the container 260. A cube-shaped interior space 261 completely encompasses the chamber 263. The space 261 has descenter 262 (e.g., but not limited to, ozone or ozone etc.) therein.

FIG. 12C shows a container 265 according to the present invention which is a sphere. A thing 269 is contained in a spherical chamber 268 within the container 265. Surrounding the chamber 268 is a space 266 with descenter 267 therein. The descenter 267 is, e.g., but not limited to, ozone or ozone etc. Any container according to the present invention (including, but not limited to, any room or enclosed space or any shown in FIGS. 11, 12A, 12C and 14A) may have any of the items, systems, and/or apparatuses shown in FIG. 12 (those inside the container and/or those outside it).

Figure 13:
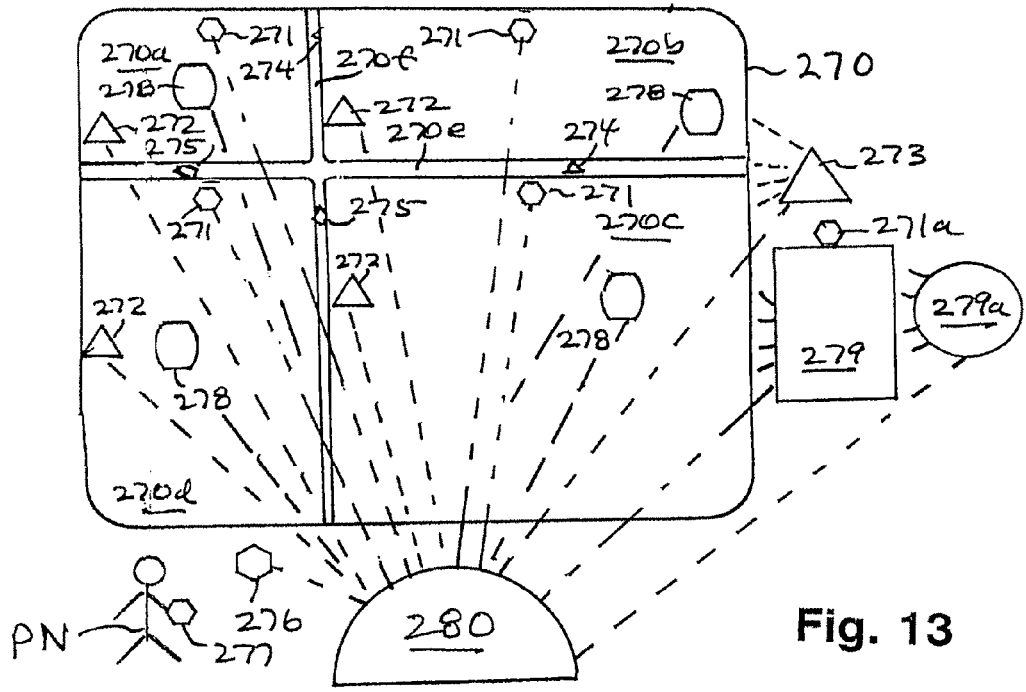
FIG. 13 is a schematic view of a system according to the present invention.
Figure 14:
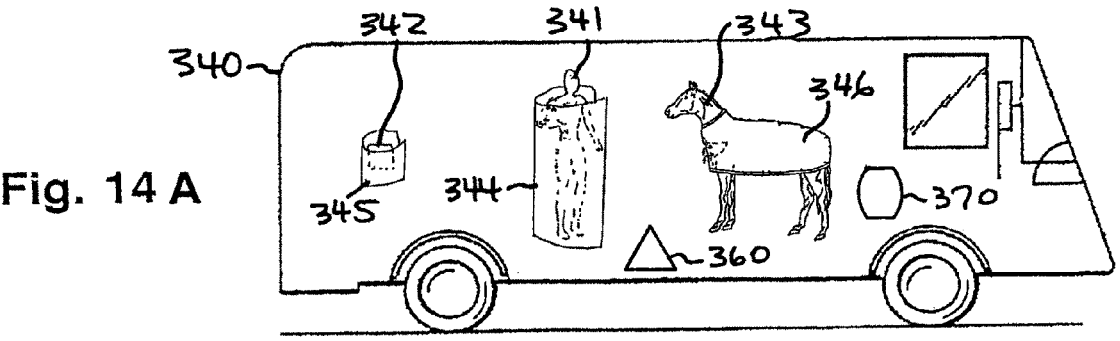
FIG. 14A is a schematic view of a vehicle with things therein wrapped according to the present invention.
FIG. 14B is a schematic view of an airplane with things therein wrapped according to the present invention.
Figure 14:
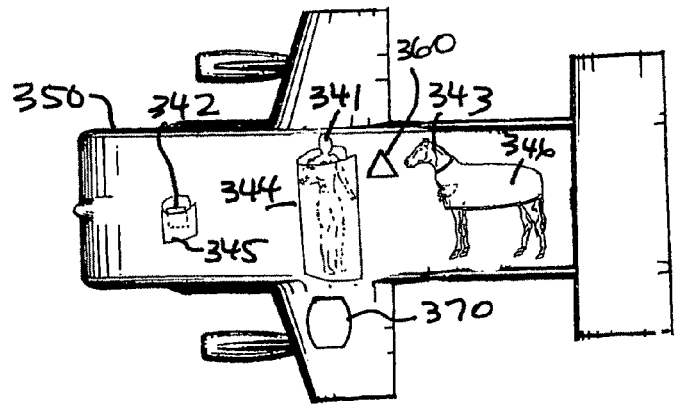

FIG. 13 shows a structure 270 with multiple rooms 270a, 270b, 270c, and 270d. At least one room or each room has a detector 271 for detecting a level of descenter, e.g., ozone etc. and/or oxidizing agent in the room and, optionally, one room or each room has a generator 272 for generating descenter, e.g., ozone etc., within the room. Optionally, (in addition to or instead of the generators 272) a generator 273 provides ozone, etc. to all rooms. Optionally corridors 270e and 270f have an oxidizing agent generator 274 and/or a detector 275. A detector 276 is, optionally, provided outside the structure 270 for detecting a level of ozone, etc. and, optionally, a person PN may use a handheld or portable detector 277.

Optionally, a room or each room has a dehydration apparatus 278 (or apparatuses). An air processing unit 279 provides heated and/or cooled air to the structure; to one, some or all rooms; and/or to one or all corridors. The unit 279 may include a fan 279a or the unit 279 may be deleted and the fan 279a provided as a separate item. A detector 271a may be provided on or adjacent the unit 279 (and/or fan 279a).

A control system 280 (e.g. like the control system 216) is in communication with and in control of each operational item and apparatus in FIG. 13.

In one method according to the present invention, a normal ambient level of descenter, e.g. ozone etc., or an abnormally low or high level is detected in the room 270c by the detector 271. The detector 271 sends a signal to the control system 280. The control system 280 stops all air flow to and from the room 270c (and, in one aspect, to and from the other rooms and corridors). In one aspect, if the detector detects an abnormally low drop in ozone level (indicating that a toxic, foreign or contraband substance has entered the room and is reacting with the ambient ozone in the room, the control system 280 stops all air flow to and from the room 270c (and, in one aspect, to and from the other rooms and corridors). In another method, a sensor senses an injurious agent within the room 270b. The sensor can be an ozone detector, a radioactive material sensor, a chemical sensor, a biological sensor, and/or any sensor that is capable of detecting a foreign, especially contraband, substance). The control system 280 isolates the room 270b; turns on the generator 272 to provide descenter, e.g. ozone, etc., into the room 270b; and, optionally, turns on the dehydration apparatus 278. Optionally, cool air is provided into the room 270b with the unit 279 and/or the generator 273 is turned on to provide ozone, etc outside the room 270b. In one aspect, when it is determined that the descenter has lowered the contraband levels to a safe level (e.g. by means of any detector), the room is optionally vented (preferably to the atmosphere, but possibly to a storage container). The room(s) may be further subjected to one or more additional additions of descenter if necessary. Any room air and/or material that is sent to a container may be further treated with oxidant or any other means and/or disposed of properly.

In any structure, enclosure, container, system, or method described above, ozone, etc. may be provided to reduce dust in air in the structure, etc.

Ozone generators of all sizes, weights, power sources and types are widely available from sources such as Sharper Image (www.sharperimage.com), Biozone Scientific (www.biozonescientific.com), Ozone Solutions (www.ozoneapplications.com) and Air Zone (www.aaaozone.com). Optionally, the ozone generator contains an additional ion generator source for negative ionization of the air. These type of units are commercially available, e.g. IONIC BREEZE (Trademark) products from Sharper Image. Optionally, the ozone generator is of the type that includes atomized water or hydrogen peroxide to produce highly reactive hydroxyl radicals. Such generators are disclosed, e.g., in Japanese patent references JP11-00948A; JP11-009949A; JP2003001/237A2; JP11-226108A; and JP 11-226106A. Optionally, the ozone generator can include the simultaneous or intermittent generation of other known oxidizing agents, bacteria and odor removing substances such as chlorine, zinc ricinoleate and/or cyclodextrine, e.g. as contained in FEBREEZE (Trademark) fabric softener. For hunting purposes it is preferable that the unit be light weight, portable, and battery and/or solar power operated and/or with a hand crank generator, e.g., when walking to a hunt. When hunting from a stationary location, such as blind or tent, it is preferable to have the same features, but if a portable generator or source of AC electric power is available, then ozone generators having this capability are also preferred. When hunting from a blind or a tent, it is still preferred to use low weight generators since the generator often needs to be transported, e.g., carried from a lodge, cabin or vehicle, e.g. to a watching or hunting location; but generators weighing up to about 8 lbs. and more may also be used. In general, light weight ozone generators produce lower levels of ozone and generate ozone for a shorter period of time, especially when small batteries such as size A, AA, AAA, C, D and 9 volt batteries are used. However, many battery operated portable ozone generators last eight hours and more on one battery charge. The ozone etc. generation source can be of any type including a UV light sources, electrical discharge, or combination of both. Certain portable, battery-operated and solar-operated ozone etc. generators have UV light as the ozone generator source due mainly to the lower voltage required for UV lamps. Larger generators capable of operating on AC current can be UV lamp, electrical discharge or a combination of both. Electrical discharge ozone generators can be capable of generating larger amounts of ozone in a smaller size container, but adding blowers, fans and transformers (which is within the scope of the present invention) can result in some generators being heavier than generators having UV lamps. Small, portable battery and solar operated ozone etc. generators are available which have small fans, though many have no fan at all. One advantage of including at least a small fan is that the ozone etc. can be dispersed over a larger area more readily, but it is not necessary that a fan be included in the ozone generator.

When treating a larger area, e.g. an area with or full of contraband, or containing a smaller amount of contraband hidden within a larger amount of legal cargo, an ozone etc. generator having a fan or fan blower is preferred, but not required. If a fan or fan blower is used, a fan can be used which makes minimum noise, especially beyond about a ten foot radius of fan operation so as not to be audibly detected by a human, handler or service animal.

For treating a larger area like a room or tent, especially when two or more persons occupy it, a generator having a fan or fan blower is preferred, but not required. If a fan or fan blower is used, a fan can be used which makes minimum noise, especially beyond about a ten foot radius of fan operation (e.g, but not limited to, so as not to spook an animal, e.g. a deer).

Certain ozone generators are capable of producing 15 mg and up to 5,000 mg/hr of ozone and more. For safety consideration, in certain embodiments of the present invention a person is exposed to a constant concentration of 0.1 ppm ozone or less and, in one aspect, such a concentration over an 8 hour time period or less; but exposures to larger concentrations up to 0.2 ppm ozone and more over short periods of time can be tolerated by most humans. One preferred ozone generator is one which can maintain about 0.1 ppm or less total ambient concentration of ozone etc. over an area of approximately a six foot radius of a human.

In other aspects, the present invention provides for a method for reducing foreign scent in a space between contraband and the service animal, the methods including producing descenting material with a material descenting generator with directional apparatus, directing said descenting material in a desired direction into the space, the directional apparatus including at least one director in communication with the generator for receiving produced descenting material from the generator and for directing said descenting material into the space, and reducing the foreign scent (i.e., the odor emanating from the contraband) in the space with the descenting material. In certain embodiments, the descenting material is ozone and the method further includes exposing the contraband to a time-weighted average value of 0.1 ppm of ozone in ambient air or less over an area within a radius of six feet of the contraband; exposing the contraband to a time-weighted value of 0.2 ppm or ozone in ambient air or less; or exposing the contraband over a time period of eight hours or less to a time-weighted value of 0.1 ppm of ozone in ambient air or less.

For humans that are avoiding an encounter with a service animal for a leisure manner, e.g., those attempting to conceal only small amounts of contraband past a handler or law enforcement officer, a small battery-powered descenting material generator, such as the BIOZONE Model 50 Personal Air Purifier, can be used. For persons attempting to conceal contraband for an extended period, e.g., an hour or more, a larger ozone generator, such as the BIOZONE SCIENTIFIC TRAVELAIRE generator, the OMZ-200 generator from Ozone Solutions or the Ozonics HR-100 ozonator from Ozonics, can be used. For those engaging in concealing larger amounts of contraband, descenting material generator, such as the Ozonics HR-100 ozonator from Ozonics, can be used. Alternatively, the OZONE SOLUTIONS Model MZ-450 or the OZONE SOLUTIONS OMZ-3400 can be used. The MZ-450 and OMZ-3400 are primarily suited for 110V A/C operation, but can alternatively be operated with for four or more hours on a single battery charge. For even higher amounts of ozone output, descenting material generators currently sold by EcoQuest International of Greeneville, Tenn., which also sells generators of hydroxyl and hydroperoxide ions, may be preferred.

As battery technology improves, it may be possible to operate high ozone concentration descenting material generators with batteries that weigh much less. The use of ozone can quickly reduce or eliminate odors (including human odors), volatiles and contaminates (all collectively referred to as "foreign scents") on a person, the person's clothing or equipment and in the space between the person and a service animal or handler.

In certain aspects the present invention provides methods for reducing foreign scent in a space between a human being and an animal, the methods including generating descenting material with a generator, introducing the descenting material into a space between a human being and an animal, the space containing foreign scent, and reducing the foreign scent in the space with the descending material. In certain embodiments, the descending material is ozone etc. and, in one particular aspect, the method further includes: exposing the human being to a time-weighted average value of 0.1 ppm ozone in air or less over an area within a radius of six feet of the human being; exposing the human being to a time-weighted value of 0.2 ppm ozone in air or less; or exposing the human being over a time period of eight hours or less to a time-weighted value of 0.1 ppm ozone in air or less. In other aspects the present invention provides methods for reducing foreign scent in a space between a human being and an animal, the methods including producing descending material with a generator, with direction apparatus, directing said descending material in a desired direction into the space, the direction apparatus including at least one director in communication with the generator for receiving produced descending material from the generator and for directing said descending material into the space, and reducing the foreign scent in the space with the descending material. In certain embodiments of such methods the descending material is ozone and the method further includes: exposing the human being to a time-weighted average value of 0.1 ppm ozone in air or less over an area within a radius of about six feet of the human being; exposing the human being to a time-weighted average value of 0.2 ppm ozone in air or less; or exposing the human being over a time period of eight hours or less to an ozone concentration of a time-weighted average value of 0.1 ppm ozone in air or less. For humans that are pursuing an encounter with an animal in a leisure manner, e.g. those hunting and producing only small amounts of odor via sweat and lighter breathing, a small battery generated ozone generator like the BIOZONE Model 50 Personal Air Purifier capable of operating on four C batteries can be used. For persons engaging in an animal-encounter activity, e.g. photography or hunting, for an extended period, e.g. an hour, two hours, three hours, four hours, or more hours, a larger ozone generator such as the BIOZONE SCIENTIFIC TRAVELAIRE (Trademark) generator weighing about 8 oz. or an OMZ-200 (Trademark) generator from Ozone Solutions weighing about 12 oz. and operating only with larger batteries or AC can be used. For those engaging in mostly stationary activity, e.g. hunting outdoors or in a tent or blind, then an ozone generator such as the OZONE SOLUTIONS Model MZ-450 can be used which is capable of deodorizing 2,000 sq. ft. with it's 450 mg/hr ozone generation and 61 cfm (cubic feet per minute) fan, or a 6 lb. OZONE SOLUTIONS OMZ-3400 having a 3,400 mg ozone output and 34 cfm fan can be used. The MZ-450 and OMZ-3400 are primarily suited for 110V operation, but can be operated with larger batteries e.g. batteries currently weighing about 4 lbs. and capable of operating for four or more hours on a single battery charge. As battery technology improves, it may be possible to operate high ozone concentration generators with batteries that weigh much less.

The use of ozone etc. can quickly reduce or eliminate odors (including human odors), volatiles, bacteria, and contaminates (all collectively referred to as "foreign scents") on a person or his or her clothing and equipment and in the space between the person and an animal that may be alerting wildlife to the presence of a human. The ozone is cleanly reduced to oxygen. The many uses of ozone that are known to kill bacteria, eliminate smoke and react with alcohols, esters, saturated organics, acyclics, aromatic, heterocyclics and more to purify the air for healthier human consumption are used in certain methods according to this invention not to purify the air for human breathing, e.g. for a hunter normally in a very clean outdoor environment, but to react with odors emitted by humans so that these volatiles are not detected by an animal, e.g. a deer. Since ozone has a half-life of minutes, airborne unreacted ozone still continues to clean bacteria, odors or clothing. In addition, any gear that has odor emanating from the gear is also cleaned. Without being bound by any theory, it is believed that in one aspect, ozone in the air kills bacteria in certain body areas, including, but not limited to, in the underarm and groin areas that is responsible for producing many of the odor-causing volatiles emitted by humans; and in another aspect, any volatile odors that are produced and emitted directly by humans via the skin are oxidized by the ozone into compounds that are much less volatile and therefore far less detectable to animals, e.g. deer. In another aspect, it is believed that any volatile odors that are produced and emitted directly by humans via the feet and escape through the shoe or socks are oxidized by the ozone into compounds that are much less volatile and therefore far less detectable to deer. In yet another aspect, it is believed that the more powerful (but much shorter life-time) hydroxyl and/or hydroperoxide radical oxidants that are produced by ozone reacting with ultraviolet rays of the sun and/or the UV lamp of an ozone generator and/or moisture in the air contribute to odor elimination.

In yet another aspect, it is believed that any pheromone or combinations of pheromones (which contain a wide variety of alcohol, ester, and saturated organic functionality) that are produced and emitted by humans at levels far to small to be detectable by humans but not by animals, e.g. deer, are oxidized by the ozone into compounds that are much less volatile and therefore far less detectable to animals, e.g. deer. In yet another aspect, it is believed that odorants in breath such as aldehydes, alcohols and acids are oxidized by the ozone into compounds that are much less volatile and therefore far less detectable to animals, e.g. deer. In yet another aspect, it is believed that it is possible that oxidized volatiles, even if they are still somewhat volatile and detected by animals, e.g. deer, are changed enough in composition that the animals, e.g. deer, no longer detects the oxidized volatiles as human.

In yet another aspect, it is believed that it is possible that higher levels of ozone in the environment around animals, e.g. deer, overpowers any human volatile such that the animals, e.g. deer, perceive the higher concentration of ozone as the result of commonly-occurring and natural lightning that may be miles away from the animals, e.g. deer.

Prior to descending of clothes, use of special soaps, shampoos and carbon and/or metal containing clothing, or combinations of these is optional, but not necessary, when using ozone for animal encounters, e.g. hunting. There is no limitation to the number of ozone generators used except for taking the precaution of not allowing a person to come into contact with an unsafe amount of ozone that affects human health. For cost and convenience, one ozone generator located on or near a person is sufficient. Multiple generators located on a person, near a person as the person is walking, inside a blind, outside of a blind, and combinations thereof, may result in an especially enjoyable activity, e.g. a hunt.

The ozone generator or generators are, in one aspect, located approximately 1-2 feet above a person's head. It is within the scope of the present invention to locate an ozone generator at a person's feet or near any part of a person's body. Heights greater than about five feet above the head may be used, but it is possible that too much dispersion of the ozone results in less ozone contacting and then eliminating odors emanating from a person to effectively prevent an animal from detecting a human or to attract an animal. In certain aspects, an ozone generator is placed in a position that is substantially upwind of a person, e.g. a hunter, and slightly elevated above the person's head such that the ozone effectively contacts and then reduces or eliminates odors emanating from the person. A descenter generator can also be hidden under clothes, or stored in luggage, a briefcase, or a backpack etc. if desired.

Referring now to FIG. 1, in one embodiment 10 of systems and methods according to the present invention an ozone generator G is located on a person P in a blind B, e.g. a hunter, especially when the person is walking to an activity site, e.g. a hunt site or engaged in an activity, e.g. hunting. The person P is wearing clothes C which may be any typical clothing or which may be any clothing disclosed herein according to the present invention.

Optionally the blind B has an interior ozone generator N and/or an exterior ozone generator R. Optionally an ozone generator T is placed outside the blind B. The person P may be outside the blind B. The blind may be a fabricated structure or a home-made blind on the ground or in a tree, e.g. made of conveniently located brush and foliage. The blind may be a unit such as an enclosure, hut, or a tent that is brought to the sight or permanently located at the site.

According to certain aspects of the present invention, there is provided a method for the de-scenting of clothing used by sportsmen by the use of an oxidizing gas, namely, ozone or by ionization with UV light to produce hydroxyl and hydroperoxide ions. More particularly, clothing is treated with ozone or the hydroxyl and hydroperoxide ions either at home or in the field by the application of a small amount of ozone or the hydroxyl and hydroperoxide ions in order to remove the human scent or any other foreign scent. Also, the clothing of fishermen can be treated with the oxidizing gas while in the field to remove the odor of fish.

According to one embodiment of the invention, the human scent can be eliminated from clothing by applying a low volume stream of an oxidizing gas comprising ozone or hydroxyl and hydroperoxide ions directly on the hunter while he is wearing a hunting outfit. The gaseous stream is applied by an ozone generator which is hand held or a catalytic ionizer containing UV light and easily transported by the hunter. The gaseous stream can be applied directly to the clothing being worn by the hunter in an open atmosphere so as to be quickly diluted after it is passed over the clothing. Moreover, the gun or rifle or any other equipment, i.e. ammunition, arrows, scope, finders etc., of the hunter or sportsmen can be similarly treated to remove the gun or rifle or equipment odor.

In accordance with another embodiment of the invention, the human scent of a military person desiring to escape detection by other humans or scent animals (e.g. dogs) is reduced or eliminated enough to avoid detection. More particularly, there is provided a method for reducing or eliminating human or any other foreign scent from clothing, e.g. clothing and equipment used by military persons desiring to evade capture—through the use of ozone or hydroxyl and hydroperoxide ions produced by ionization in a manner that would not cause irritation or injury to the user or equipment.

In accordance with another embodiment of the invention, the clothing of the hunter can be treated before or after the hunt by placing the clothing in a container i.e. a sack, bag or box while passing the oxidizing gas into the container in order to remove any human or other scent foreign to that environment.

Another embodiment of the invention is that the generator is carried with a hunter or hung upwind of the body so it descents the human scent traveling downwind. In another embodiment of the invention, the generator is carried or placed with or near a hunter with little or no regard to wind direction, allowing for a full 360 degree hunt.

Also, some certain clothing is not cleaned after every use by the hunter or sportsmen such as gloves, hats, jackets, boots, and need to be deodorized and decontaminated before next use.

According to a further embodiment of the invention, the odor of fish can be eliminated from a fisherman's clothing, body or equipment by the direct application of a stream of ozone gas or hydroxyl and hydroperoxide ions to the site of the fish odor. Additionally, a fisherman's hands can be deodorized with ozone so as to remove the fish odor without causing irritation.

Each of the methods can be practiced in the open in the field of sports activity utilizing a low volume gas generator. The clothing is not decolorized as in applications involved in high volumes of ozone as found in the garment industry where ozone is used to both de-size and/or decolorize denim garments. The oxidizing gas may be used alone or diluted with air as when packaged in a compressed gas form. Ozone which is produced by generators in amounts up to 8000 mg/hr or more can be compressed or diluted with an inert gas and compressed into small containers.

It is understood that the term "sportsmen" is meant to include those individuals who may hunt with a camera or who merely enter an environment to observe animals in their habitat.

Additionally, the term "fishermen" includes those individuals who handle the fish caught by others.

Hydroxyl and hydroperoxides are produced in a process known as "Radiant Catalytic Ionization" which utilizes ultra violet light which activates a photocatalytic target.

Small ozone generators such as those producing 1 to 25 lbs. of ozone per day can be utilized. Also the ozone can be applied from compressed ozone-filled containers similar to compressed air.

Low volume ozone generators which generate up to 65 mg/hr of ozone and are portable as well as high volume ozone generators are currently sold by EcoQuest International of Greeneville, Tenn. which also sells the generators of hydroxyl and hydroperoxide ions.

It will be appreciated by persons skilled in the art that numerous variations and/or modifications may be made to the invention without departing from the spirit or scope of the invention as broadly claimed.

The present invention discloses methods of reducing or of eliminating any scent that is foreign to the environment from the clothing, equipment and body of sportsmen, by generating a volume of ozone gas or a gaseous stream of hydroxyl and hydroperoxide ions produced by catalytic ionization and passing the gas over the clothing, body, or equipment. Such a method may include any of the following: wherein said scent is human scent or any other scent that is not natural to the environment; passing said gas over a gun or rifle of said sportsman; wherein said sportsman is a hunter; wherein said scent is fish odor; wherein said gas is generated by a hunter at the field of the hunt; wherein the clothing is treated with said gas while being worn by the sportsmen; wherein said clothing and equipment is treated with said gas when in a container; wherein said gas is ozone; wherein said gaseous stream is produced by catalytic ionization; and/or wherein said gas is compressed and delivered from a container. The present invention discloses a method for removing the human scent and any other scent that is not advantageous to the environment you are in from clothing and equipment used by sportsmen by the use of gaseous ozone or hydroxyl and hydroperoxide ions. The gas is applied directly or indirectly to the clothing, equipment and body while the hunter is in the field and/or prior to or after the hunt. The method can also be used by fishermen to eliminate fish odor. The method can include delivering a gas in compressed/generated form from a generator that is a container.

The following Examples further illustrate the invention, but are not intended to be limiting thereof. In these examples ozone concentration monitoring was done with an OS-4HIGH RANGE (Trademark) ozone sensor from Eco Sensors, Inc. of Santa Fe, N. Mex.

EXAMPLES

For any example it would be within the scope of the present invention to use an ozone etc. generator.

Example I shows how ozone reduces underarm odor from humans.

Examples II-X show how ozone reduces odors associated with human antiperspirants and perfumes.

Examples XI-XII show how ozone can eliminate odors in a tent or blind.

Examples XIII-XXVII show how ozone can eliminate odors from cloth, rags, and clothes placed in a container (e.g. garment bag, luggage, or cooler) and treated with ozone.

Example XXVII shows how ozone treatment results in an improved hunting experience.

Example I

Ozone from a DC PRO 450 HO (Trademark) generator was directed to the underarm of a human for a period of 30 seconds. The odor before treating with ozone was a 10 on a personal odor scale ("POS") scale in which bad odor is at worst a "10" and reduced odor is less than 10, and after treatment the odor was a less than 1 on the POS scale.

Example II

Stick deodorant, Right Guard EXTREME (Trademark) deodorant, was wiped onto the back of a human hand. The odor from the deodorant before treating with ozone was a 10. After 5 minutes treatment with ozone using the DC PRO 450 HO ozonator within 12 inches of the hand, the smell was very faint (<1 on the POS scale).

Example III

Male cologne, Calvin Klein's OBSESSION FOR MEN™ cologne, was sprayed twice on the back of a human hand. The odor before treating with ozone was a 10. After four minutes treatment with ozone using the DC PRO 450 HO (Trademark) ozonator within 12 inches of the hand the smell was very faint (<1 on the POS scale).

Example IV

Example III was repeated but the cologne was sprayed only once on the back of a human hand. The odor before treating with ozone was a 10. After 5 minutes treatment with ozone using the DC PRO 450 HO (Trademark) ozonator, the smell was very faint (<1 on the POS scale).

Example V

Human hands had smoke and cigarette smell thereon from campfire and lighting of cigarette. The odor before treating with ozone was a 10. After 2 minutes treatment with ozone using the DC PRO 450 HO (Trademark) ozonator the smell was very faint (<1 on the POS scale).

Example VI

A human rubbed both hands liberally with a sliced onion and placed hands in front of a DC PRO 450 HO (Trademark) ozonator. The odor before treating with ozone was a 10. After two minutes treatment with ozone, the smell was gone (0 odor).

Example VII

A human rubbed fresh crushed garlic on both hands and placed one of the hands in front of DC PRO 450 HO (Trademark) ozonator (within 12 inches). The odor before treating with ozone was a 10. After two minutes and 20 seconds treatment with ozone the smell was faint (less than 1 on the POS scale). After six minutes the smell negligible, and after eight minutes the smell was gone (0 odor). By comparison, the hand not treated with ozone remained a 10 (on the POS scale) after eight minutes.

Example VIII

A human rubbed MAGIC BAIT (Trademark) bait (chicken liver and chicken blood combination on both hands and placed one of the hands in front of the DC PRO 450 HO (Trademark) ozonator (within 12 inches). The odor before treating with ozone was a 10 (on the POS scale). After ten minutes the hand treated with ozone had about a 2 odor (on the POS scale). By comparison, the hand not treated with ozone remained a 10 (on the POS scale) after ten minutes.

Example IX

A human rubbed an ORKA BAY WILD COD (Trademark) fillet on both hands and placed one of the hands in front of DC PRO 450 HO (Trademark) ozonator (within 12 inches). The odor before treating with ozone was a 10. After seven minutes the hand treated with ozone had a 1 odor (on the POS scale). By comparison, the hand not treated with ozone remained a 10 (on the POS scale) after ten minutes.

Example X

A back of a human hand was sprayed with two sprays of Ralph Lauren ROMANCE (Trademark) perfume. The odor before treating with ozone was a 10 (on the POS scale). After five minutes treatment with ozone using the ozonator the smell was faint (2 odor on the POS scale).

Example XI

Placed Glade CINNAMON APPLE PLUG-INS SCENTS (Trademark) in two tents, each with a volume of about 125 cubic feet. After 2 hours, the smell in both tents was a 10 (on the POS scale). In one tent a BIOZONE DC PRO 3400 (Trademark) ozonator was turned on. At the time intervals stated below, the odor level (on the POS scale) in the tents was as follows:

| 10 minutes | |
|---|---|
| Ta | 10 |
| Tb | 6 |
| 20 minutes | |
| Ta | 10 |
| Tb | 5 |
| 30 minutes | |
| Ta | 10 |
| Tb | 4 |
| 45 minutes | |
| Ta | 10 |
| Tb | 0 |

(Ta = Tent without ozone; Tb = Tent with ozone)

Example XII

Placed Air Wick TROPICAL MIST PLUG INS (Trademark) on plug-in control set at a setting of MAX ODOR in a tent with a PRO 3400 (Trademark) ozonator with an Eco Sensors sensor; and in a second "control" tent with no ozonator, placed an Air Wick TROPICAL MIST PLUG INS (Trademark) on plug-in control set at a setting of MAX ODOR with all tent doors and flaps closed. After 30 minutes both tents had 10 odor (on the POS scale). Then the ozonator with the plug-ins at a control setting of MAX ODOR, was turned on and ozone levels in the tent with the ozonator rose as follows (with odor levels in both tents, on POS scale, as indicated):

```
0 minutes = 0.00 ppm
1 minute = 0.26 ppm
2 minutes = 0.50 ppm
3 minutes = 0.71 ppm
4 minutes = 0.87 ppm
5 minutes = 1.02 ppm      (odor in ozonated tent, 4; in control
                           tent, 10)
15 minutes = 2.43 ppm     (odor in ozonated tent, 3; in control
                           tent, 10)
21 minutes = 2.35 ppm     (odor in ozonated tent, 3-4; in control
                           tent, 10)
At 21 minutes, turned output of both plug-ins to a 0.5 control
setting.
31 minutes = 2.42 ppm
36 minutes = 2.34 ppm     (odor in ozonated tent, 4; control tent,
                           10)
41 minutes                (unplugged both plug-ins and removed from
                           tents)
56 minutes = 2.97 ppm     (odor in ozonated tent, 1; control tent,
                           10)
71 minutes                (set both plug-ins on a "low" control
                           setting in each tent
81 minutes = 2.81 ppm     (odor in ozonated tent, 1; control tent,
                           10)
```

Example XIII

An ENVIROSORB (Trademark) cellulose solvent pillow (available from Lab Safety Supply, Inc.) was saturated with butyl mercaptan vapors by placing an open bottle of butyl mercaptan in a closed metal paint can containing the pillow. The vapor-saturated pillow was then placed in a DILLARD'S (Trademark) garment bag along with a DC PRO 450 HO (Trademark) ozonator. The odor before treating with ozone was a 10 (on the POS Scale). After 20 minutes with the ozonator on in the bag, treated imbiber had a smell of 1 on the POS scale.

Example XIV

Approximately 0.5 ml of butylmercaptan was added to 10 ml denatured alcohol in a SEP (Trademark) commercial sprayer. Five sprays of the mixture were sprayed on a cotton t-shirt. The shirt was placed in a garment bag along with a DC PRO 450 HO (Trademark) ozonator. The odor before treating with ozone was a 10 (on the POS Scale). After 20 minutes treating with ozone in the bag, the treated shirt had a smell of 2 on the POS scale and a control shirt (no treatment) had a smell of 10 on the POS scale.

Example XV

Ralph Lauren ROMANCE (Trademark) fragrance was sprayed twice on a cotton shirt and placed in the garment bag of Example XIII along with a DC PRO 450 HO (Trademark) ozonator. The control shirt was sprayed two times with the fragrance and placed in open air. The odor on both shirts before treating with ozone was a 10 (on the POS scale). After 10 minutes of ozone treatment in the bag, the treated shirt had a smell of 0 and the control shirt had a smell of 10.

Example XVI

One spray of LEMON FRESH PINESOL (Trademark) liquid was sprayed on each of two cloths. One cloth was placed in the garment bag of Example XIII with a DC PRO 450 HO (Trademark) ozonator, and the other cloth (control) was placed outdoors. The odor on both cloths before treating with ozone was a 10 (on the POS scale). After 6 minutes of ozone treatment in the bag the treated cloth had a smell of 0 on the POS scale and the control cloth had a smell of 2 on the POS scale.

Example XVII

Smoke from a small fire of had and small twigs was allowed to permeated 2 cloths. One cloth was placed in the garment bag of Example XIII with a DC PRO 450 HO (Trademark) ozonator and the other cloth (control) was placed outdoors. The odor on both cloths before treating with ozone was a 10 (on the POS scale). After 5 minutes of treating with ozone, the treated cloth had a small of 0 on the POS scale and the control cloth had a smell of 6 on the POS scale.

Example XVIII

Smoke from a lit cigarette was blown into two cloths. One cloth was placed in the garment bag of Example XIII with DC PRO 450 HO (Trademark) ozonator, and the other cloth (control) was placed outdoors. The odor on both cloths before treating with ozone was a (on the POS scale). After 6 minutes of treating with ozone in the bag, the treated cloth had a 0 smell on the POS scale and the control cloth had a smell of 6 on the POS scale.

Example XIX

Ralph Lauren ROMANCE (Trademark) fragrance was sprayed twice on the outside of a SCENT-LOK SAVANNAH EXT (Trademark) jacket. At time=0, the smell of the sprayed jacket was a 10 on the POS scale. After 5 minutes in the open air the smell was still an 8 on the POS scale. The jacket was then placed in the garment bag of Example XIII with a PRO 3400 (Trademark) ozonator. After treating the jacket for 10 minutes in the bag with ozone the smell was a 2 on the POS scale. After 15 minutes of ozone treatment in the bag the odor of the jacket was a 1 on the POS Scale. After 20 minutes of such treatment the odor was gone.

Example XX

The inside lining of a jacket as in Example XIX was sprayed with the ROMANCE (Trademark) fragrance and placed inside the bag of Example XIII with a PRO 3400 (Trademark) ozonator. At time=0, the smell was a 10 on the POS scale. After treating the jacket for 5 minutes in the bag with ozone the smell was a 3 on the POS scale. After 10 minutes of ozone treatment in the bag the odor of the jacket was a 1-2 on the POS scale. After treating the jacket for 15 minutes in the bag with ozone the smell was a 0-1 on the POS scale. After 20 minutes the odor was gone.

Example XXI

ROMANCE (Trademark) fragrance was sprayed onto two cloth rags with four sprays of the fragrance each. One cloth was placed in a bag as in Example XIII with a PRO 3400 (Trademark) ozonator and the other cloth (control) was placed outside. At time=0, the smell on both rags was a 10 on the POS scale. After 5 minutes the ozone-treated rag was a 0 on the POS scale and the outside cloth was a 2 on the POS scale.

Example XXII

Two rags were each sprayed with two sprays of Calvin Klein OBSESSION FOR MEN (Trademark) cologne plus four sprays of the Ralph Lauren ROMANCE (Trademark) fragrance. One rag was placed in a bag as in Example XIII with a PRO 3400 (Trademark) ozonator and the other rag was placed outside. At time=0, the smell on both rags was a 10 on the POS scale. After 5 minutes of treatment, the ozone cloth in the bag had a smell of 0 on the POS scale and the cloth outside had a smell of 10 on the POS scale.

Example XXIII

The OBSESSION (Trademark) cologne was sprayed (2 sprays) on two SCENT-LOK SAVANNAH EXT coats. One coat was placed in a bag as in Example XIII with a PRO 3400 (Trademark) ozonator. The other coat (control) was placed in the open air. The results are below:

| TIME<br>CONTROL COAT SMELL<br>COAT TREATED WITH OZONE<br>(SMELLS ON POS SCALE) |
| --- |
| 0 minutes |
| 10<br>10<br>5 minutes |
| 10<br>7 |
| 7 minutes |
| 10<br>4<br>13 minutes |
| 8<br>3<br>18 minutes |
| 7<br>2 |

(e.g. at 7 minutes the control coat had a smell of 10 and the treated coat had a smell of 4)

Example XXIV

The OBSESSION (Trademark) fragrance was sprayed (2 sprays) each onto one sweat shirt, one camouflage t-shirt (short sleeved), one camouflaged long-sleeved t-shirt, one pair of denim jeans, one cotton short pants and one cotton t-shirt. All the clothes were placed in a bag as in Example XIII in no order along with a PRO 3400 (Trademark) ozone generator. The smell at time=0 in the bag was a 10 on the POS scale. After 95 minutes treatment with ozone in the bag, each garment had a less than 1 smell on the POS scale. Ten hours later, all the clothes placed in the bag still had ozone odor on them. At this time all the clothes were placed in an unsealed plastic bag and another 14.5 hours later the clothes still had ozone odor on them.

Example XXV

One spray of COON URINE (Trademark) Hunter's Masking Scent was sprayed onto a t-shirt. The t-shirt was placed into a bag as in Example XIII along with a BORA IV LIVING AIR (Trademark) ozonator (fan on max). The results are shown below for the indicated number of minutes of treatment with ozone in the bag:
0 minutes=10 odor (odor of shirt on POS scale)
5 minutes=6 odor
10 minutes=2 odor
15 minutes=1 odor Example XXVI One spray of the OBSESSION (Trademark) cologne was sprayed onto a POLAR TEC (Trademark) fleece jacket and placed into a 150 quart cooler fitted with a clothes rod and hanger. The fleece jacket was placed on the hanger and a PRO 3400 (Trademark) ozone generator was placed into the cooler. The smell at time=0 in the cooler was a 10 on the POS scale. After 15 minutes treatment with ozone, the garment had about a 1 smell on the POS scale.

Example XXVII

On spray of the OBSESSION (Trademark) cologne was sprayed on a green long-sleeved shirt (100% cotton knit) and placed in the cooler as described in Example XXVI along with a PRO 3400 (Trademark) generator. A small fan was placed in the bottom of the cooler and turned on max with the fan facing up. The smell at time=0 in the cooler was a 10 on the POS scale. After 15 minutes of treatment with ozone in the cooler, the shirt had about a 1 smell on the POS scale. Then the shirt was re-placed in the cooler and treated with ozone for an additional 30 minutes. This resulted in several red streaks on the shirt due to the ozone contacting and remaining on the shirt. The shirt was then removed from the cooler and placed on a table open to the ambient air. About eleven hours later, the shirt still had an ozone smell and almost all the red streaking had disappeared. Another 12 hours later minimal ozone smell was noticeable and all red streaking had disappeared.

Example XXVIII

A sweaty t-shirt that a human jogged in for 3.5 miles over 35 minutes was placed on a hanger in the cooler of Example XXVI along with a PRO 3400 (Trademark) ozone generator and a small fan in the cooler was turned on high. The smell at time=0 in the cooler was a 10 on the POS scale. After 20 minutes treatment with ozone in the cooler, the garment had about a 2 smell on the POS scale.

Example XXIX

A hunter placed himself in a cedar bush located in the Fort Peck Wilderness Area in Montana. A Biozone 50 (Trademark) battery-operated ozonator was placed on a backpack located between the hunter's legs and turned on. An elk was observed approaching within 8 yards of the hunter about 45 minutes after the ozonator was turned. The elk passed downwind and through the hunter's scent line without detecting the hunter.

Example XXX

A hunter placed himself in a home-made blind of native brush in South Texas along with an OMZ-200 (Trademark) battery operated ozonator hung from the blind and located about 10 inches behind and above his head. The hunter did not use any SCENT-LOK (Trademark) clothing, masks or scents prior to or during the hunt, but was camouflaged using Cabela's lightweight ghillie pants, jacket and facemask. Deer corn was placed at the perimeter of the blind going out to about 30 feet from the blind. Within 10 minutes of turning on the ozonator to Max Setting, up to 6 white tail deer at a time and several birds (cardinals and finch) were observed feeding within 10 yards downwind of the hunter in a 3 hour time span. One young buck was observed within 5 feet downwind of the blind where the hunter was laying. None of the deer, cardinals or finch appeared to have scented the hunter.

Optionally, a feeder FR is provided to attract an animal (e.g., but not limited to, a grain feeder for attracting a deer or a bird feeder for attracting a bird). Any known feeder may be used, including but not limited to, an automatic powered timed feeder. An ozone generator X connected to or adjacent the feeder FR produces ozone to descent the feeder, the feed, and/or the area around the feeder.

In all the Examples I-XXX the ozonator or generator included a fan as part thereof and this fan was operating when the ozonator or generator was turned on.

Figure 2:
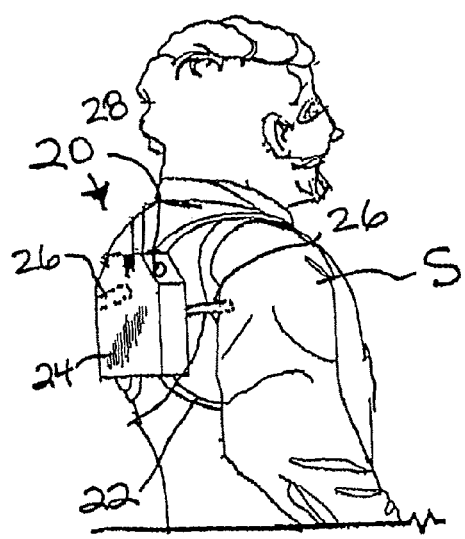
FIG. 2 is a perspective view of a system according to the present invention.

FIG. 2 shows a person S with an over-shoulder removable harness 22 of a system 20 according to the present invention. An ozone generator 24 is connected to the harness 22. Optionally produced ozone is directed to the person's underarms by tubes 26. Optionally, produced ozone is expelled from the ozone 24 via a port 28.

Figure 3:
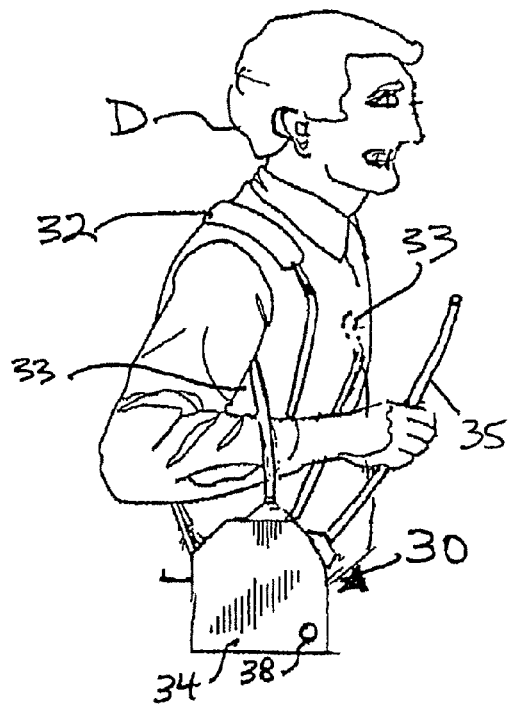
FIG. 3 is a perspective view of a system according to the present invention.

FIG. 3 shows a person D with a system 30 according to the present invention. A shoulder strap 32 supports an ozone generator 34. Optionally produced ozone is expelled through a port 38. Optionally tubes 33 direct produced ozone to the person's underarms. Optionally the system 30 includes a free tube 35 which may be of any desired length and which is movable and/or flexible for directing ozone to any body part and/or toward any item or area.

Figure 4:
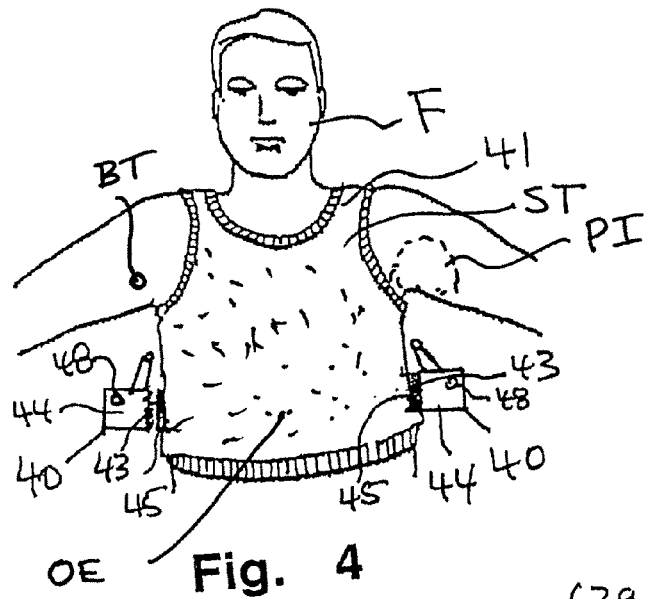
FIG. 4 is a front view of a system according to the present invention.

FIG. 4 shows two systems 40 according to the present invention used by a person F. Each system 40 has an ozone generator with a nozzle 46 for directing produced ozone in a desired direction at a desired body part. Each system 40 has thereon an amount of releasably-cooperating hook-and-loop fastener material 43. A corresponding amount 45 of this material is on a shirt 41 of the person F; thus, the ozone generators 44 are releasably connected to the shirt 41. Optionally, such a connection can be provided for any ozone generator disclosed herein for connection to any piece of clothing, footwear, blind, or other item. Optionally each ozone generator 44 has a produced-ozone exit port 48. The person F is wearing clothing, including a shirt ST.

It is within the scope of the present invention to provide descenter (e.g. ozone or ozone etc.) at a body part or area adversely affected by an encounter with a rash-inducing and/or irritation inducing substance, animal, or plant (e.g., but not limited to) poison ivy or stinging nettle) or an area affected by a bug, spider, wasp, bee, ant, or insect bite. In one aspect, descenter is directed at such an area, e.g. ozone is directed from an ozone generator, e.g. as in FIG. 4 ozone is directed at an area PI irritated by poison ivy or at a bite BT using one of the generators of FIG. 4.

Figure 5:
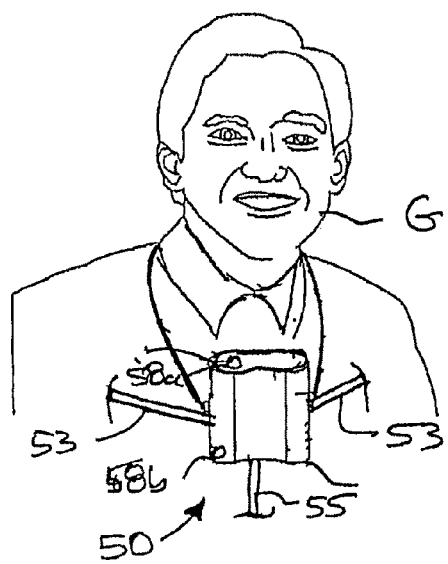
FIG. 5 is a front view of a system according to the present invention.

FIG. 5 shows a person G with a system 50 according to the present invention with an ozone generator 54 worn or a string or cord 51 around the person's neck. Optionally, the system has two tubes 53, one directed to each of the person's underarms. Optionally the system 50 has a tube 55 directed to a body area beneath the person's chest (e.g. but not limited to, to the groin area). Optionally, the ozone generator 54 has a produced-ozone exit port 58a and/or a produced-ozone exit port 58b.

Figure 6:
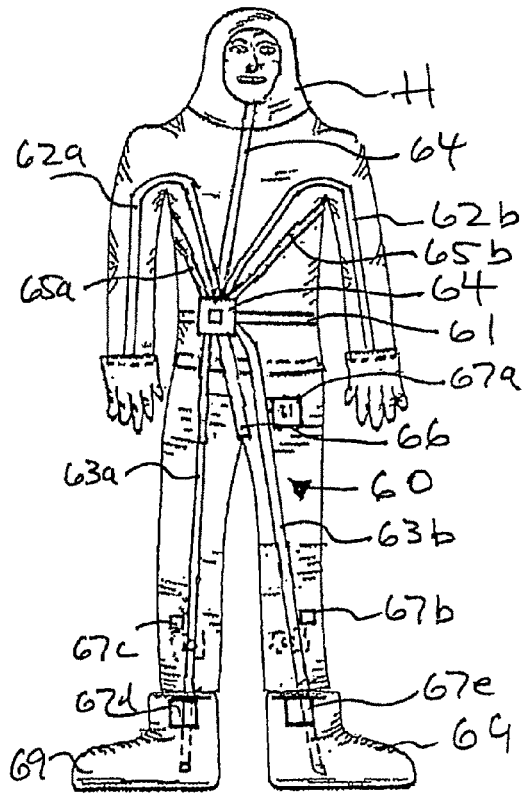
FIG. 6 is a front view of a system according to the present invention.

FIG. 6 shows a person H with a system 60 according to the present invention having an ozone generator 64 worn around the waist on a belt 61. It is within the scope of the present invention for the belt to be around any body part or area (e.g. but not limited to, head, arm, leg, chest, foot). Tubes 62a, 62b, 63a, 63b, 64, 65a, 65b, and 66 extend to various body parts or areas to convey ozone to those parts or areas. Optionally, an ozone generator or generators 67a, 67b, 67c, 67d, and/or 67e may be used with or instead of the ozone generator 64. The tubes 63a, 63b can, as shown extend down into boots 69 or they can be terminated above the boots 69.

FIG. 7 shows a system 80 according to the present invention with an ice chest or cooler 71 with an openable lid 71a and body 71b with an interior space 71c. Shown schematically within the interior space 71c is an ozone generator 72, an optional fan 73, a piece of cloth 74 and an item 75 (shown schematically, may be any thing that will fit within the cooler, including, but not limited to, any item or thing disclosed herein which can be descented with ozone). With the lid 71a closed or open, the ozone generator is turned on to produce ozone to descent the cloth 74 and/or the item 75. When the optional fan 73 is present and turned on, it provides air to circulate the ozone. It is within the scope of the present invention for the ozone generator 72 and the fan 73 to be powered via an electrical power source (not shown) using a typical electrical power cord (not shown); or, as shown, the ozone generator 72 and the fan 73 are battery-operated. Optionally, or in addition to the fan 73, a fan 73a may be used outside the cooler 71 with the lid 71a open.

A cooler according to the present invention may, optionally, have at least one zone, space, layer or area located between the inside and outside of the cooler where oxidant (e.g. ozone) is present or directed. The cooler may optionally be made of a material that absorbs or contains ozone and may also change color to indicate the presence or absence of ozone. The ozone not only reduces or eliminates the odors from the contents within the cooler, but also may reduce germs and bacteria for the cooler and the contents within the cooler.

FIG. 8 shows a system 80 according to the present invention with a flexible bag 81 with an openable zipper 81a and body 81b with an interior space 81c. Shown schematically within the interior space 81c is an ozone generator 82, an optional fan 83, a piece of cloth 84 and items 85, 86, 87 (shown schematically, may be any thing that will fit within the bag, including, but not limited to, any item or thing disclosed herein which can be descented with ozone). With the zipper 81a closed or open, the ozone generator is turned on to produce ozone to descent the cloth 84 and/or the item 85. When the optional fan 83 is present and turned on, it provides air to circulate the ozone. It is within the scope of the present invention for the ozone generator 72 and the fan 73 to be powered via an electrical power source or solar power source (not shown) using a typical electrical power cord (not shown); or, as shown, the ozone generator 72 and the fan 73 are battery-operated. Optionally, or in addition to the fan 83, a fan 83a may be used outside the flexible bag 81, with the zipper 81a open or closed.

The bag may optionally have at least one zone, layer, space, or area located between the inside and outside of the bag where oxidant (e.g. ozone) may be present or directed. The bag may optionally be made of material that absorbs or contains ozone and may also change color to indicate the presence or absence of ozone. The ozone not only reduces or eliminates the odors from the contents within the container, but also may reduce germs and bacteria for the bag and the contents within the bag. In one embodiment, the bag may contain food. In another embodiment the bag may contain a human body (e.g. body bag).

FIGS. 9A and 9B show a system 90 according to the present invention which includes a portable container 92 with a hinged lid 96 connected with hinges 98 to a main body 91. As shown in FIG. 9B (with the lid 96 open) the interior of the container can contain a plurality of items, e.g., but not limited to, diving gear F, G, H, J. An ozone generator 94 is placed within the container 92 and, with the lid 96 open or closed, the ozone generator 94 produces ozone to descent the items F-J. It is within the scope of the present invention for the ozone generator 72 and the fan 73 to be powered via an electrical power source or solar power source (not shown) using a typical electrical power cord or solar cell (not shown); or, as shown, the ozone generator 72 and the fan 73 are battery-operated.

The portable container may optionally have at least one zone, space, layer, or area located between the inside and outside of the container where oxidant (e.g. ozone) may be present or directed. The container may optionally be made of a material that absorbs or contains ozone and may also change color to indicate the presence or absence of ozone. The ozone not only reduces or eliminates the odors from the contents within the container, but also may reduce germs and bacteria for the container and the contents within the container. In one embodiment, the container may contain food. In another embodiment the container may contain a human body.

FIGS. 10A and 10B show a system 100 according to the present invention which includes a garment bag 102 with handles 101a and 101b and an interior space 101c. The garment bag 102 may contain any thing or item that will fit therein. As shown schematically in FIG. 10B, the garment bag 102 contains items of clothing 103, 104 hung therein and shoes 105. An ozone generator 106 is placed within the garment bag 102 to produce ozone to descent the items therein. Optionally a fan 107 is also used within the garment bag 102. It is within the scope of the present invention for the ozone generator 72 and the fan 73 to be powered via an electrical power source (not shown) using a typical electrical power cord (not shown); or, as shown, the ozone generator 72 and the fan 73 are battery-operated. Optionally, or in addition to the fan 107, a fan 107a may be used outside the bag 102 with the bag 102 open or closed.

The garment bag may optionally have at least one zone, space, layer, or area located between the inside and outside of the bag where oxidant (e.g. ozone) may be present or directed. The garment bag may optionally be made of a material that absorbs or contains ozone and may also change color to indicate the presence or absence of ozone. The ozone not only reduces or eliminates the odors from the contents within the bag, but also may reduce germs and bacteria for the bag and the contents within the bag. In one embodiment, the bag may contain food. In another embodiment the bag may contain a human body (e.g. a body bag).

It is to be understood for any embodiment disclosed herein that mentions an "ozone generator" that a descenting material generator may be used that produces ozone, etc. and/or any, each of, and/or all descenting materials referred to herein and their equivalents, with or without an integrated fan that is operating. In the systems of FIG. 2-FIG. 10A any suitable ozonator, ozone generator, or descenting material generator may be used, with or without a fan that is operating.

Without being bound by any theory, it is believed that in one aspect, ozone in the air kills bacteria in certain body areas of humans, including in the underarm and groin areas—areas responsible for producing many of the odor-causing volatiles emitted by humans. In another aspect, volatile odors produced and emitted directly by humans via the skin, mouth or feet are oxidized by ozone into compounds that are much less volatile and therefore far less detectable to service animals. In another aspect, it is believed that ozone in the air substantially reacts with volatiles in the air emitted by the contraband so that the scent is below the level of detection by the service animal. In yet another aspect, it is believed that the more powerful (but much shorter life-time) hydroxyl and/or hydroperoxide radical oxidants, produced by ozone reacting with ultraviolet rays and/or moisture in the air, contribute to odor elimination.

Without being bound by theory, it is believed that in one aspect, ozone reacts with the residue or exposed surface of the contraband to produce an oxidized substance that has no odor or that is no longer volatile and therefore not detectable by the service animal or human. In another aspect, any volatile odors that are produced and emitted directly by the contraband are reacted with the gaseous ozone to produce an oxidized substance that has no odor or that is no longer volatile and therefore not detectable by the service animal or human. In another aspect, it is believed that ozone in the air kills the bacteria in the underarm and groin area that is responsible for the odor-causing volatiles emitted by human and animal contraband. In another aspect, any volatile odors that are produced and emitted directly by human or animal contraband via the skin are oxidized by the ozone into compounds that are much less volatile and therefore less detectable to humans and service animals. In another aspect, any volatile odors that are produced and emitted directly by human or animal contraband via the feet and escape through the shoe or socks are oxidized by the ozone into compounds that are much less volatile and therefore less detectable to humans and service animals. In yet another aspect, any pheromone or combinations of pheromones (which contain a wide variety of alcohol, ester, and saturated organic functionality) that are produced and emitted by human and animal contraband at levels far too small to be detectable by humans but not by service animals, are oxidized by the ozone into compounds that are much less volatile and therefore far less detectable to service animals. In yet another aspect, odorants in breath of human and animal contraband such as aldehydes, alcohols and acids are oxidized by the ozone into compounds that are much less volatile and therefore far less detectable to humans and service animals. In yet another aspect, it is possible that oxidized volatiles of contraband, even if they are still somewhat volatile and detected by humans and service animals, are changed enough in composition that the human or service animal no longer detects the oxidized volatiles as human or animal contraband. In yet another aspect, it is possible that higher levels of ozone in the environment around the contraband overpowers any odor volatiles such that the service animal or human perceives the higher concentration of ozone as the result of commonly-occurring and natural lightening.

In all systems and methods according to the present invention, there is no limitation to the number of generators used except for taking the precaution of not allowing human or animal contraband to come into contact with an unsafe amount of descenter, e.g., ozone etc. that adversely affects human health and one, tow, or more such generators may be sued in any system or method according to the present invention. For cost and convenience, one generator located on, in or near contraband is sufficient in many cases. Multiple generators located on, in or near the contraband, and combinations thereof, may result in better concealment of the contraband from the law enforcement officer or service animal.

In systems and methods according to the present invention, oxidizing gas may be used alone or diluted with air as when packaged in a compressed gas form. Ozone etc., which is produced by generators in amounts up to 8000 mg/hr or more, can be compressed or diluted with an inert gas and compressed into small containers.

Example A

A person climbed a tree in the woods near his house and turned on an Ozonics HR-100 ozonator. A neighbor's dog walked by some time later. When directly downwind the dog stopped, sniffed, looked confused, but walked on. When he came to where the person had walked into the woods he stopped and sniffed the person's trail for a few feet then left and continued on his way. The dog did not detect that the person was in the tree.

Example B

A narcotics test was performed using 4 different Police trained dog handlers and their trained narcotics dogs. Latex gloves were placed on the hands of anyone handling the narcotics, cardboard boxes, and Ozonics HR-100 ozone generators used in this demonstration so that the trained dogs would not be influenced by the scent of a human.

In a room was placed five legal sized cardboard boxes spaced approximately 2 to 3 feet apart from one another. In a random order was placed 1 small bag of cocaine wrapped in plastic into a box. Into another box was placed a small bag of heroin wrapped in plastic that contained an HR-100 ozonator that was turned on. Into another box was placed just an HR-100. Two boxes had nothing in them. After putting lids on each box and then 10 minutes of running the ozonators, one Police officer and their dog at any given time entered the room. The Police officer instructed their dog to search each of the boxes. All the dogs identified the box containing the cocaine almost immediately by scratching the box and then laying down in front of the box. The dogs were immediately rewarded by their handler by opening the box to show the plastic wrapped cocaine and giving praises to their dogs. It took several attempts for the four dogs to detect the heroin masked by the ozone, and all had to be instructed by their handlers to put their nose into the carrying holes of the cardboard box to detect the heroin. None of the dogs reacted to the box containing just the ozonator.

It will now be appreciated by anyone skilled in the art that ozone etc. can unexpectedly be used to conceal contraband from service animals having been trained to detect small amounts of odor from contraband that humans cannot generally detect.

Unfortunately, contraband is routinely smuggled into sovereign countries and entities in which it is illegal to possess, such as the United States. Consequently, law enforcement personnel have a vested interest in breaking the smuggling procedure. Taking advantage of the innate acuteness of service animals such as contraband-sniffing canines, law enforcement personnel have routinely used such canines on the front line of defense against the smugglers. However, the smugglers have been known to use a wide variety of substances and devices to especially mask the odor associated with the narcotic contraband, including coffee grounds. Once enforcement personnel were alerted to the smugglers use of coffee grounds to mask narcotics, the narcotics personnel then trained their dogs to detect the use of coffee grounds as a mask for the narcotics. The new use for systems and methods according to the present invention provide law enforcement personnel with an added level of defense in their struggle against the contraband smugglers attempting to use ozone based descenters to eliminate or reduce the odor of contraband.

For the new use, a plurality of packages are provided, wherein at least one package contains a predetermined amount of contraband. Preferably, the amount of contraband is enough to be detected by the contraband-detecting canines. Further, a scent remover (descenting generator, e.g., similar to any described herein with regard to the present invention) is placed in or near at least one of the packages, and operated to remove the odor emanating from the contraband. Additionally, "dummy" packages—packages containing nothing—may be disposed in the area as well. Optionally, at least one package can contain just an ozone-based scent remover.

A service animal, such as a contraband-detecting canine, is then introduced to the area in which the packages are located. In time, and relying on the superior olfactory sense of the animal, the service animal will be able to detect which package(s) contain contraband, which package(s) contain contraband masked by the scent remover, which package(s) contains just a generator (or ozonator), and which package(s) contain nothing. Training of the contraband-detecting canine to detect the various packages is preferably done according to known training techniques. To assist in the training of the service animal, rewards are typically provided, in the form of food and/or praise, to the animal for a successful detection.

To further aid in the successful detection of a person attempting to use a descenting system to conceal contraband, the handler may optionally posses a descenter, e.g. an ozone etc., detection device to confirm the presence of descenter, e.g. of ozone etc., above the normal ambient concentration of ozone etc. The detection device may be any that are well known in the art such as a badge, test strip, gas detector (available from UV Process Supply, Chicago Ill. www.uvprocess.com), or sensor such as the Ecosensor PO3 pocket ozone detector or Ecosensor EZ-1x ozone monitor available from Ecosensor (www.ecosensors.com). In this way, the handler can confirm for example, that the concentration of ozone etc. is elevated in one particular area compared to an area just a short distance away from the area of interest. This may provide the handler with the evidence needed to obtain a search warrant to investigate further. Alternatively, if the smuggler is present, the handler could show the result to the smuggler and request that the smuggler turn off any descenting device so that the service animal can then positively detect any contraband.

The detector may have a probe or tube to allow for poking the probe or tube into various depths of the containers, enclosures, trailers, hidden areas, etc., to detect the presence of abnormally high levels of oxidant (e.g. ozone). The detector may optionally also have an input at, in, or very near the detector to also measure ambient oxidant (e.g. ozone) levels so that a difference of ambient oxidant versus an abnormally higher level of oxidant (e.g. ozone) can be better compared and detected.

In many cases contraband, especially airborne contraband, and contraband contained in water supplies and soil, can adversely affect the health and property of humans and animals. This is especially true of narcotics, radioactive materials and wastes, toxins and biological agents/weapons such as viruses, anthrax, botulinum toxin, aflatoxin, *Salmonella Typhimurium, Ascaris suum, B. anthracis*, ricin, plague, smallpox and more such as is described in the Department of Health and Human Services Centers for Disease Control and Prevention Emerging Infectious Diseases Journal, "Potential Biological Weapons Threats", located at http://www.cdc.gov/ncidod/EID/vol5no4/kortepeter.htm. Application of ozone etc. to especially airborne, soil, or water containing contraband in concentrations sufficient to effectively reduce or eliminate the contraband will reduce the health and safety aspects of the contraband upon the health and property (including clothing) of humans and animals. Whether the contraband was discovered after attempted concealment of the contraband with ozone etc., or was detected by other means, including visual means, application of descenter, e.g. of ozone etc., or of additional ozone etc. at or near the contraband effectively reduces or eliminates injurious effects of the contraband and reduces or eliminates the negative health and safety aspects of the contraband upon the health and property of humans and animals. When humans and animals are present in the vicinity of contraband, especially airborne contraband, application of descenter, e.g. of ozone etc., at or in the vicinity of the human so that the human is contacted by, takes in, or breathes ozone etc. results in injurious effects of contacted or inhaled contraband also being effectively reduced or eliminated in the nose, mouth, respiratory tract, lungs, and even blood of the human or animal.

Example C

A person came into contact with poison ivy on their ankle and had red, itchy skin. Ozone from an Ozonics HR-100 ozone generator was directed at the ankle for about 20 minutes. Shortly thereafter, the skin was still red, but the skin no longer itched, and the poison ivy was observed not to extend beyond the original area of skin that was already red.

It is recognized that especially narcotic and toxic contraband such as the biological contraband mentioned above is a serious criminal and terrorist threat, especially to people and to the people and property of government buildings, public buildings, subways, airports, buses, sporting arenas and the like. Once narcotic or toxic contraband is detected by any means, at or near the contraband, application of additional descenter, e.g., ozone etc., will effectively reduce or eliminate injurious effects of the contraband will reduce the health and safety aspects of the contraband upon the health and property of humans and animals. The application of ozone etc. can be manual, or automated via detection of the contraband by any means, including electronic detection of the contraband by well know instrumentation known in the art such as infrared and UV instruments. In one aspect an ozone detector is used that measures reduction of ambient ozone below normal levels since this indicates reaction of the ambient ozone with a foreign substance (e.g. contraband) that likely should not be present. If the injurious effects are on or are caused on the skin of a human or animal, descenter can be directed at the injured skin, or a material containing absorbed descenter may be placed directly on or near the skin. In this way, injurious effects of harmful contraband on skin can be neutralized, and harmful contraband can be prevented from re-exposing injured skin. The descenter also provides for the reduction and killing of germs and bacteria from contacting and/or entering injured skin, resulting in a better prognosis for the human or animal. The material can be of the type that changes color to indicate when descenter is present or absent from the material. If the public area or building has air ducts, descenter, e.g. ozone etc., could also be applied via the air ducts manually or automatically to decontaminate at least a portion of the area containing the contraband. If the public area or building has air duct(s), descenter, e.g. ozone etc., is also applied via the air duct(s) manually or automatically to decontaminate at least a portion of the area containing the contraband.

The present invention, therefore, provides in certain, but not necessarily all embodiments, a system and method for reducing or eliminating the various odors that are detectable by service animals, and to the detection, by those animals, of such systems and methods.

In other aspects, according to the present invention, a descenting system described herein is used to train contraband-detecting service animals to determine if a system, is or has been used in an attempt to reduce or eliminate the scent of contraband.

In other aspects, in systems and methods according to the present invention, descenter, e.g., ozone etc., is used to reduce or eliminate especially airborne narcotic and toxic contraband to protect the health and safety of humans and animals, protect humans that have breathed the narcotic or toxic contraband, and to decontaminate public buildings and public areas and the people contained in these areas to the narcotic or toxic contraband.

In certain aspects of the present invention, a blanket, piece of clothing, gauze, fabric, or wrap has descenter, e.g. ozone etc., bound within it and/or absorbed therein. For example, the clothing worn by the person F in FIG. 4 includes a shirt ST that has bound to its material an oxidant OE (any ozone etc. bindable to or absorbable by the material of the shirt). Any piece of clothing according to the present invention can have such a bound or absorbed oxidant.

FIG. 15 illustrates a blanket 300 according to the present invention which is made of fabric 302. Bound to or absorbed into the material of the fabric 302 is oxidant (or descenter) 304 (shown grossly as dots and not to scale in FIG. 15) which can be any oxidant bindable to the material. Optionally, the oxidant 304 is oxidant that has been absorbed by the material of the fabric 302. For the text descriptions of the subject matter of FIGS. 15-18, "descenter" may be used for "oxidant."

FIG. 16 shows a person 301 wrapped in a blanket 310 which is like the blanket 300, FIG. 15. The blanket 310 has oxidant (or descenter) 314 bound to the material of its fabric 312 or absorbed therein. Wrapping the person in the blanket can mask odors from the person and can inhibit the effectiveness of discovery by animals trained to smell humans, human odors, and/or smells associated with humans such as food smells, deodorant smells, and soap smells and the like. The oxidant 314 is shown grossly and not to scale as in FIG. 15.

The blanket, wrap, cloth having descenting material described above is, optionally, a bandage material, wound dressing material, or a gauze material that is useful for covering a cut, abrasion or wound to any part of the body of a human or animal, in this way helping the healing of the person be reacting with foreign substances in and around the cut, abrasion, or wound, eliminating or reducing odor emanating therefrom, and/or reducing or eliminating germs and bacteria from entering or spreading to or on the cut, abrasion or wound. The blanket, wrap, cloth, etc., material is, optionally, color changing material to indicate the presence or relative absence of descenting material contained on or in the material.

FIG. 17 shows an animal, a horse 321, wrapped in a blanket 320 which is like the blankets 300 and 310. The blanket 320 has oxidant (or descenter) 324 bound to the material of its fabric 322 or absorbed therein. Wrapping the horse in the blanket can mask odors from the horse and can inhibit the effectiveness of discovery by animals trained to smell humans. The oxidant 324 is shown grossly and not to scale as in FIG. 15. Any animal can be wrapped in a blanket or wrap according to the present invention. Any person or animal can, according to the present invention, be clothed and/or wrapped totally or only partially with a clothing, blanket or wrap according to the present invention.

FIG. 18 shows a thing 331 wrapped in a wrap 330 according to the present invention. The wrap 310 has oxidant 334 bound to its material 332 or absorbed therein. Wrapping the thing in the wrap can mask odors from the thing and can inhibit the effectiveness of discovery by animals (including humans) and discovery by animals trained to smell such things. Wrapping the thing in the wrap can mask odors from the thing so that humans cannot smell it. The oxidant (or descenter) 334 is shown grossly and not to scale as in FIG. 15.

FIG. 14A shows a vehicle 340 according to the present invention that has therein a person 341, a thing 342, and/or an animal 343. The person 341 is wrapped in a blanket 344 (like the blanket 300 or 310). The thing 342 is wrapped in a wrap 345 (like the wrap 330; or like any blanket according to the present invention). The animal 343 is wrapped in a blanket 346 (like the blanket 300 or the blanket 310). Any of the person 341, thing 342, and animal 343 may be contraband.

FIG. 14B shows an airplane 350 according to the present invention that has therein a person 341, a thing 342, and/or an animal 343 (like those in FIG. 14A and like numerals indicate like things). The person 341 is wrapped in a blanket 344 (like the blanket 300 or 310). The thing 342 is wrapped in a wrap 345 (like the wrap 330; or like any blanket according to the present invention). The animal 343 is wrapped in a blanket 346 (like the blanket 300 or the blanket 310). Any of the person 341, thing 342, and animal 343 may be contraband.

The vehicle 340 or the plane 350 may have an on-board descenter or ozone etc. generator 360 and/or an on-board dehydrating apparatus 370.

The present invention, therefore, provides in certain, but not necessarily all embodiments, a method for reducing foreign scent in a space between a human being and an animal, the method including: generating descenting material with a generator, introducing the descenting material into a space between a human being and an animal, the space containing foreign scent, and reducing the foreign scent in the space with the descenting material. Such a method may include one or some, in any possible combination, of the following: the foreign scent including human odor; exposing the human being to about 0.1 ppm ozone, or less, over an area, e.g. within a radius of six feet or less of the human being; exposing the human being to 0.2 ppm ozone, or less; exposing the human being to ozone produced by the generator over a time period, e.g. over a time period of eight hours or less, and 0.1 ppm, or less (all "ppm" ozone levels are a time-weighted average value in air); the descenting material being ozone and the human being has on an item of clothing and the item of clothing receives an amount of ozone produced by the generator, the amount of ozone sufficient so that ozone is retained on the item of clothing and, in one aspect, the item of clothing is colored and the ozone changes the color of at least part of the item of clothing, and the clothing is, e.g., made of knit fabric, cotton fabric, cotton blended fabric, fibrous fabric or fleece, natural fabric, synthetic fiber fabric, plastic cloth material, plastic fabric material, and/or plastic flexible material; the descenting material being ozone; the descenting material being any of ozone, hydroxy radicals, hydroperoxides, and oxidants; generating the descenting material as a gas; generating the descenting material in a mist; the human being being a hunter and the animal is an animal hunted by the human being; at least one item in the space, the item having an item foreign scent, the method further including descenting the item foreign scent; the foreign scent including human odor, the method further including supporting the generator on the human being; at least one direction apparatus in communication with the generator, the method further including with the at least one direction apparatus, directing descenting material from the generator in a desired direction; the foreign scent including human odor, the method further including supporting the generator on the human being, wherein there is at least one direction apparatus in communication with the generator, the method further including with the at least one direction apparatus, directing descenting material from the generator in a desired direction at a part of the human being; the part of the human being any of an armpit, torso, head, mouth, nostrils, groin, and feet; the at least one direction apparatus being a plurality of direction apparatuses; the foreign scent being in a blind and the descenting material introduced into the blind; the foreign scent being in a tent and the descenting material introduced into the tent; the foreign scent being any of human odor, volatile material, and contaminating material; the fan apparatus assisting in introducing the descenting material into the space; and/or the fan apparatus being spaced apart from the generator or integral therewith.

The present invention, therefore, provides in certain, but not necessarily all embodiments, a method for descenting foreign scent from an item, the method including: placing an item in a container, the item having a foreign scent, the container containing air, the container located outdoors; generating descenting material in the container with a generator; moving air in the container with a fan apparatus; and reducing the foreign scent with the descenting material; and, in certain aspects, such a method wherein: the descenting material being ozone and the human being has on an item of clothing and the item of clothing receives an amount of ozone produced by the generator, the amount of ozone sufficient so that ozone is retained on the item of clothing; the item of clothing being colored and the ozone changes the color of at least part of the item of clothing; and the fan apparatus is spaced apart from the generator or is integral therewith.

The present invention, therefore, provides in certain, but not necessarily all embodiments, a system for descenting human odors on an item, the system including: a container; a descenting material generator in the container; and a fan apparatus in the container for moving air in the container as descenting material is produced by the descenting material generator.

The present invention, therefore, provides in certain, but not necessarily all embodiments, a system for reducing foreign scent in a space between a human being and an animal, the system including a generator for producing descenting material; and at least one direction apparatus (or a plurality of them) in communication with the generator for receiving produced descenting material from the generator and for directing said descenting material in a desired direction to reduce the foreign scent.

The present invention, therefore, provides in certain, but not necessarily all embodiments, a method for reducing foreign scent in a space between a human being and an animal, the method including: producing descenting material with a generator; with direction apparatus, directing said descenting material in a desired direction into the space, the direction apparatus including at least one director in communication with the generator for receiving produced descenting material from the generator and for directing said descenting material into the space; and reducing the foreign scent in the space with the descenting material. Such a method may include one or some, in any possible combination, of the following: the descenting material is ozone and the method further including exposing the human being to about 0.1 ppm ozone, or less, over an area within a radius of about six feet of the human being; the descenting material is ozone and the human being is exposed to a concentration of 0.2 ppm ozone, of less; the descenting material is ozone and the human being over a time period of eight hours or less is exposed to an ozone concentration of only 0.1 ppm or less.

The present invention provides, in certain aspects, methods for directing descenter to a wound, etc., to kill germs and/or facilitate healing.

It is within the scope of the present invention, in circumstances in which an animal (to include a human being) has been exposed to the injurious effects of material or animals (including, but not limited to, the injurious effects of contraband) for the animal (e.g., but not limited to any animal in any of FIGS. 1-6, 11, 13-14B, 16, and/or 17) to intentionally breathe in descenter (e.g., but not limited to, ozone) to reduce or eliminate the injurious effects (e.g. on airways, nasal passages, nose, throat, lungs, mouth and blood).

The present invention, therefore, provides in certain, but not necessarily all embodiments, a method for detecting presence of a thing, the thing treated with a descenter, the method including: in an area in which it is possible that a thing treated with a descenter is present, using a detector to detect a descenter level in the area, producing a detected descenter level; comparing the detected descenter level to a normal descenter level for the area; and determining that the detected descenter level is above the normal descenter level, said determining indicating the possible presence of a thing treated with a descenter. Such a method may include one or some, in any possible combination, of the following: generating descenter in the area with a descenter generator following a determination that the detected descenter level is less than the normal descenter level; wherein an enclosure with an enclosure interior is in the area and a thing treated with descenter is possibly within the enclosure, the method further including: ventilating the interior of the enclosure; generating descenter in the enclosure with a descenter generator following a determination of the detected descenter level; generating descenter outside the enclosure with a descenter generator following a determination of the detected descenter level; said descenter detector being hand-holdable, a person holding the descenter detector to detect said detected descenter level; wherein the detector is sensor apparatus controlled by and in communication with a control system, the method further including with the sensor apparatus detecting a descenter level in the area and communicating said level to the control system, and then with the control system, doing said determining; wherein the enclosure is one of a container, part of a vehicle, part of a plane, and part of a truck; wherein the thing is one of at least one animal, at least one item, and at least one person; wherein the thing is contraband; following a determination of the detected descenter level, searching the area for a thing treated with descenter; wherein the searching is done with a service animal trained to locate a thing treated with descenter; wherein the service animal is trained to smell contraband and the thing treated with descenter is contraband; finding a thing treated with descenter, at least part of said thing wrapped in a member containing descenter; wherein the member is one of cloth, blanket, fabric, and wrap; wherein the member changes color to indicate the presence or absence of descenter contained on or within the article; determining the normal descenter level; adding descenter to the area to facilitate agglomeration and descent due to gravity of dust in the area; wherein the descenter is one of ozone, ozone saturated in organic solvent, hydroxyl radicals, hydroperoxide radicals, negatively charged metal oxides, hydrogen peroxide, encapsulated ozone, metastable oxygen, activated ozone, peracetic acid, chlorine dioxide, oxygen and its radicals, thixotropic gels, singlet oxygen, UV light at 254 nm, UV light at 185 nm, hypochlorite, and chlorite; and/or wherein the descenter is one of ozone, hydroxyl radicals, and hydroperoxide radicals.

The present invention, therefore, provides in certain, but not necessarily all embodiments, a container for containing a thing, the container including: a body; an interior space in the body sized for location therein of the thing; at least one secondary space in the body around and spaced apart from the interior space; and the at least one secondary space containing descenter. Such a container may include one or some, in any possible combination, of the following: including the thing, the thing in the container; wherein the thing is contraband; wherein the body is made of material that changes color in response to a descenter; and/or wherein the container is one of cooler, bag, garment bag, and body bag.

The present invention, therefore, provides in certain, but not necessarily all embodiments, a method for transporting a thing, the method including: placing a thing in a container, the container having a body, an interior space in the body sized for location therein of the thing, at least one secondary space in the body around and spaced apart from the interior space, and the at least one secondary space containing descenter, and moving the container from a first location to a second location.

The present invention, therefore, provides in certain, but not necessarily all embodiments, a method for transporting a thing, the method including while moving a thing, applying descenter adjacent the thing; and wherein the thing is contraband.

The present invention, therefore, provides in certain, but not necessarily all embodiments, a method for training a service animal to detect a thing treated with descenter, the method including: placing a service animal in an area in which a thing treated with descenter is present, and following choice of the thing by the service animal, rewarding the service animal.

The present invention, therefore, provides in certain, but not necessarily all embodiments, a method for detecting possible presence of a toxin in an area, the method including: detecting a normal level of descenter in an area, detecting an abnormal level of descenter in the area, and a difference between the normal level and the abnormal level corresponding to a change in level due to reaction of descenter with a toxin.

The present invention, therefore, provides in certain, but not necessarily all embodiments, a method for treating a bodily injury, the method including directing descenter to a bodily injury.

The present invention, therefore, provides in certain, but not necessarily all embodiments, a method for reducing effects of injurious substances, the method including following exposure to an injurious substance, inhaling descenter.

The present invention, therefore, provides in certain, but not necessarily all embodiments, a treatment member including a body of material, the material having descenter thereon or therein, and the descenter able to kill living toxin.

The present invention, therefore, provides in certain, but not necessarily all embodiments, a method for treating an area, the method including detecting a drop in descenter level in an area below a normal ambient level, and adding descenter to the area.

In conclusion, therefore, it is seen that the present invention and the embodiments disclosed herein and those covered by the appended claims are well adapted to carry out the objectives and obtain the ends set forth. Certain changes can be made in the subject matter without departing from the spirit and the scope of this invention. It is realized that changes are possible within the scope of this invention and it is further intended that each element or step recited in any of the following claims is to be understood as referring to the step literally and/or to all equivalent elements or steps. The following claims are intended to cover the invention as broadly as legally possible in whatever form it may be utilized. The invention claimed herein is new and novel in accordance with 35 U.S.C. §102 and satisfies the conditions for patentability in §102. The invention claimed herein is not obvious in accordance with 35 U.S.C. §103 and satisfies the conditions for patentability in §103. This specification and the claims that follow are in accordance with the requirements of 35 U.S.C. §112. The inventors may rely on the Doctrine of Equivalents to determine and assess the scope of their invention and of the claims that follow as they may pertain to apparatus and/or methods not materially departing from, but outside of, the literal scope of the invention as set forth in the following claims. All patents and applications identified herein are incorporated fully herein for all purposes. It is the express intention of the applicant not to invoke 35 U.S.C. §112, paragraph 6 for any limitations of any of the claims herein, except for those in which the claim expressly uses the words 'means for' together with an associated function. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

What is claimed is:

1. A method for detecting presence of a thing, the thing treated with a descenter, the method comprising in an area in which a thing treated with a descenter is present, using a detector to detect a descenter level in the area, producing a detected descenter level, comparing the detected descenter level to an initial descenter level for the area, the initial descenter level determined without the thing in the area, and determining that the detected descenter level is above the initial descenter level, said determining indicating the presence of the thing treated with a descenter, the thing being one of persons, drugs, explosives, produce, animals, agricultural products, and biological materials including bacteria, molds, dander, protein, urine, plasma, sera, viral agents, viruses, yeast, air pollen, blood, spores, protozoa, allergens, semen, radioactive materials, soil, sludge water, ground water, VOCs, biological toxins, chemical toxins, cysts, and gaseous agents.

2. The method of claim 1 further comprising generating descenter in the area with a descenter generator following a determination that the detected descenter level is less than the initial descenter level.

3. The method of claim 1 wherein an enclosure with an enclosure interior is in the area and a thing treated with descenter is within the enclosure, the method further comprising ventilating the interior of the enclosure.

4. The method of claim 3 further comprising generating descenter outside the enclosure with a descenter generator following a determination that the detected descenter level is lower than the initial descenter level.

5. The method of claim 1 further comprising said descenter detector being hand-holdable, a person holding the descenter detector to detect said detected descenter level.

6. The method of claim 1 wherein the detector is sensor apparatus controlled by and in communication with a control system, the method further comprising with the sensor apparatus detecting a descenter level in the area and communicating said level to the control system, and then with the control system, doing said determining.

7. The method of claim 3 wherein the enclosure is one of: a container, part of a vehicle, part of a plane, and part of a truck.

8. The method of claim 1 wherein the thing is one of contraband persons, contraband drugs, contraband explosives, contraband produce, contraband animals, contraband agricultural products, and contraband biological materials including contraband bacteria, contraband molds, contraband dander, contraband protein, contraband urine, contraband plasma, contraband sera, contraband viral agents, contraband viruses, contraband yeast, contraband air pollen, contraband blood, contraband spores, contraband protozoa, contraband allergens, contraband semen, contraband radioactive materials, contraband soil, contraband sludge water, contraband ground water, contraband VOCs, contraband biological toxins, contraband chemical toxins, contraband cysts, and contraband gaseous agents.

9. The method of claim 1 further comprising following a determination that the detected descenter level is above the initial descenter level, searching the area for a thing treated with descenter.

10. The method of claim 9 wherein the searching is done with a service animal trained to locate a thing treated with descenter.

11. The method of claim 10 wherein the service animal is trained to smell contraband and the thing treated with descenter is one of contraband persons, contraband drugs, contraband explosives, contraband produce, contraband animals, contraband agricultural products, and contraband biological materials including contraband bacteria, contraband molds, contraband dander, contraband protein, contraband urine, contraband plasma, contraband sera, contraband viral agents, contraband viruses, contraband yeast, contraband air pollen, contraband blood, contraband spores, contraband protozoa, contraband allergens, contraband semen, contraband radioactive materials, contraband soil, contraband sludge water, contraband ground water, contraband VOCs, contraband biological toxins, contraband chemical toxins, contraband cysts, and contraband gaseous agents.

12. The method of claim 1 further comprising finding a thing treated with descenter, at least part of said thing wrapped in a member containing descenter.

13. The method of claim 12 wherein the member changes color to indicate the presence or absence of descenter contained on or within the thing.

14. The method of claim 1 further comprising determining the initial descenter level.

15. The method of claim 1 further comprising adding descenter to the area to facilitate agglomeration and descent due to gravity of dust in the area.

16. The method of claim 1 wherein the descenter is one of ozone, ozone saturated in organic solvent, hydroxyl radicals, hydroperoxide radicals, negatively charged metal oxides, hydrogen peroxide, encapsulated ozone, metastable oxygen, activated ozone, peracetic acid, chlorine dioxide, oxygen and its radicals, thixotropic gels, singlet oxygen, UV light at 254 nm, UV light at 185 nm, hypochlorite, and chlorite.

* * * * *